US008642052B2

(12) United States Patent
Serizawa et al.

(10) Patent No.: US 8,642,052 B2
(45) Date of Patent: Feb. 4, 2014

(54) CERAMIDE DISPERSION AND METHOD FOR PRODUCING SAME

(75) Inventors: Shinichiro Serizawa, Ashigarakami-gun (JP); Hisahiro Mori, Ashigarakami-gun (JP); Tomoko Tashiro, Ashigarakami-gun (JP); Yoshisada Nakamura, Ashigarakami-gun (JP); Jun Arakawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 161 days.

(21) Appl. No.: 13/121,354

(22) PCT Filed: Sep. 30, 2009

(86) PCT No.: PCT/JP2009/067105
§ 371 (c)(1),
(2), (4) Date: Mar. 28, 2011

(87) PCT Pub. No.: WO2010/038814
PCT Pub. Date: Apr. 8, 2010

(65) Prior Publication Data
US 2011/0182999 A1 Jul. 28, 2011

(30) Foreign Application Priority Data
Sep. 30, 2008 (JP) .................................. 2008-255079

(51) Int. Cl.
*A61K 9/00* (2006.01)
(52) U.S. Cl.
USPC ........................................................ 424/400
(58) Field of Classification Search
None
See application file for complete search history.

(56) References Cited

U.S. PATENT DOCUMENTS

| 5,661,118 | A | | 8/1997 | Cauwet et al. |
| 5,679,357 | A | * | 10/1997 | Dubief et al. ................. 424/401 |
| 6,946,138 | B2 | * | 9/2005 | Iwai et al. ..................... 424/401 |
| 2002/0010215 | A1 | | 1/2002 | Shiroyama et al. |
| 2004/0228882 | A1 | | 11/2004 | Qiu et al. |
| 2004/0234566 | A1 | | 11/2004 | Qiu et al. |
| 2005/0113322 | A1 | * | 5/2005 | Bennett et al. .................. 514/44 |
| 2005/0152865 | A1 | * | 7/2005 | Yamamoto et al. ........ 424/70.23 |
| 2006/0210522 | A1 | * | 9/2006 | Ishida et al. ............... 424/70.27 |
| 2008/0182910 | A1 | | 7/2008 | Qiu et al. |

FOREIGN PATENT DOCUMENTS

| CN | 1114681 A | 1/1996 |
| CN | 1784205 A | 6/2006 |
| CN | 1822893 A | 8/2006 |
| JP | 7-187987 A | 7/1995 |
| JP | 8-059443 A | 3/1996 |
| JP | 9-124432 A | 5/1997 |
| JP | 11-310512 A | 11/1999 |
| JP | 2000-051676 A | 2/2000 |
| JP | 2001-139796 A | 5/2001 |
| JP | 2001-316217 A | 11/2001 |
| JP | 2004-331595 A | 11/2004 |
| JP | 2005-002018 A | 1/2005 |
| JP | 2006-335692 A | 12/2006 |
| JP | 2007-516067 A | 6/2007 |

OTHER PUBLICATIONS

De Vries et al. Journal of the American Oil Chemists Society 1963 40:184-186.*
Office Action dated Jul. 9, 2013 in Japanese Patent Application No. 2010-531900.
First Office Action, dated Feb. 4, 2013, issued in corresponding CN Application No. 200980138471.6, 12 pages in English and Chinese.
Office Action dated Sep. 9, 2013 in Chinese Application No. 200980138471.6.

* cited by examiner

*Primary Examiner* — Juliet Switzer
*Assistant Examiner* — Caralynne Helm
(74) *Attorney, Agent, or Firm* — Sughrue Mion, PLLC

(57) ABSTRACT

The present invention provides a ceramide dispersion which includes (1) ceramide-containing particles which contains a ceramide, which are dispersed in an aqueous phase as an oil-phase component, and which have a volume average particle diameter from 1 nm to 100 nm; and (2) a fatty acid component which is at least one of a fatty acid having a melting temperature not higher than 30° C. or a fatty acid salt; the amount of nonionic surfactant being 0 or not more than 0.1 times the total mass of the ceramide; the amount of an ionic surfactant other than the fatty acid component being 0 or less than 0.05 times the total mass of the ceramide; and the pH being from 6 to 8.

11 Claims, 2 Drawing Sheets

CERAMIDE DISPERSION AND METHOD FOR PRODUCING SAME

CROSS REFERENCE TO RELATED APPLICATION

This application is a National Stage of International Application No. PCT/JP2009/067105 filed Sep. 30, 2009, claiming priority based on Japanese Patent Application No. 2008-255079, filed Sep. 30, 2008, the contents of all of which are incorporated herein by reference in their entirety.

TECHNICAL FIELD

The present invention relates to a ceramide dispersion and a method for producing the ceramide dispersion.

BACKGROUND ART

Ceramide is present in a stratum corneum of the skin and constructs a lipid barrier necessary for retaining water, and thereby it plays an important role for maintaining moisture. Ceramide in a stratum corneum is produced by degradation of cerebroside with an enzyme called cerebrosidase. It is known that a part of ceramide is changed into phytosphingosine and sphingosine with an enzyme called ceramidase, and they are important as an agent of regulating proliferation and differentiation of cells. In a human skin, seven kinds of ceramides are present, and have different functions, respectively.

However, since ceramide is a substance having high crystallizability, has low solubility in other oil solution, and precipitates a crystal at a low temperature, it was difficult to maintain stability when incorporated into cosmetics. Further, an aqueous ceramide dispersion may be dispersed using surfactants, but it is difficult to make a particle diameter of an dispersion sufficiently small, and thereby the dispersion inferior in transparency may be produced in some cases.

An emulsified composition that contains a specific group of sphingoglycolipid having moisturing effect, preventing effect on chapped skin, and emulsifying effect is disclosed as a composition containing ceramide (for example, refer to Japanese Patent Application Laid-Open (JP-A) No. 2000-51676).

A cosmetic additive combined with ceramide which contains cholesterol, fatty acid, and water-soluble polymer (for example, refer to JP-A No. H07-187987) is disclosed. As a composition for external use which is excellent in stability under rapidly changing temperature conditions and has good after-use feel, a water-in-oil type emulsified composition obtained by using sphingosines salt formed with a specific fatty acid as an emulsifying agent and adding an oil-soluble antioxidant at a specific ratio (for example, refer to JP-A No. 2006-335692) is disclosed.

As pharmaceutical preparation technique, a method for producing an additive agent for cosmetic in which a crude dispersion solution of sphingoglycolipid is microparticulated using a specified jet flow in order to sufficiently exhibit the emollient effect of sphingoglycolipid is disclosed (for example, refer to JP-A No. 11-310512).

On the other hand, a process for blending specific fatty acids and specific surfactants is disclosed as a technique for transparently solubilizing and stably blending ceramide (for example, refer to JP-A Nos. 2001-139796 and 2001-316217). However, in order for the ceramide to be made transparent and solubilized, it is necessary to increase the amount of surfactant to be added, and therefore, safety and a sense of use may be compromised. On the other hand, if a small amount of surfactant is added in order to obtain a superior sense of use, the ceramide often becomes cloudy or in a translucent milky state and cannot be made transparent and solubilized. In such a case, separation or creaming over time of the ceramide occurs, and it is difficult to secure a sufficient stability over time of the ceramide.

Thus, even by using these technique, it is, at present, not possible to obtain a ceramide dispersion in which the ceramide can be stably dispersed and which has a superior stability over time.

DISCLOSURE OF THE INVENTION

Means for Solving the Problems

An object of the present invention is to provide a ceramide dispersion in which ceramide-containing particles having a very small particle diameter are stably dispersed and which has a superior stability over time.

The present invention provides a ceramide dispersion and a method for producing the ceramide dispersion.

A first aspect of the present invention provides a ceramide dispersion including: (1) ceramide-containing particles which contains a ceramide, which are dispersed in an aqueous phase as an oil-phase component and which have a volume average particle diameter from 1 nm to 100 nm; and (2) a fatty acid component which is at least one of a fatty acid having a melting temperature not higher than 30° C. or a fatty acid salt, the amount of a nonionic surfactant being 0 or not more than 0.1 times the total mass of the ceramide; the amount of an ionic surfactant other than the fatty acid component being 0 or less than 0.05 times the total mass of the ceramide; and the pH being from 6 to 8.

The second aspect of the present invention provides a method for producing the ceramide dispersion, the method including mixing an oil phase component containing at least the above-mentioned ceramide with an aqueous phase component at a temperature not higher than 40° C.

MODE FOR CARRYING OUT THE INVENTION

[Ceramide Dispersion]

Figure 1:
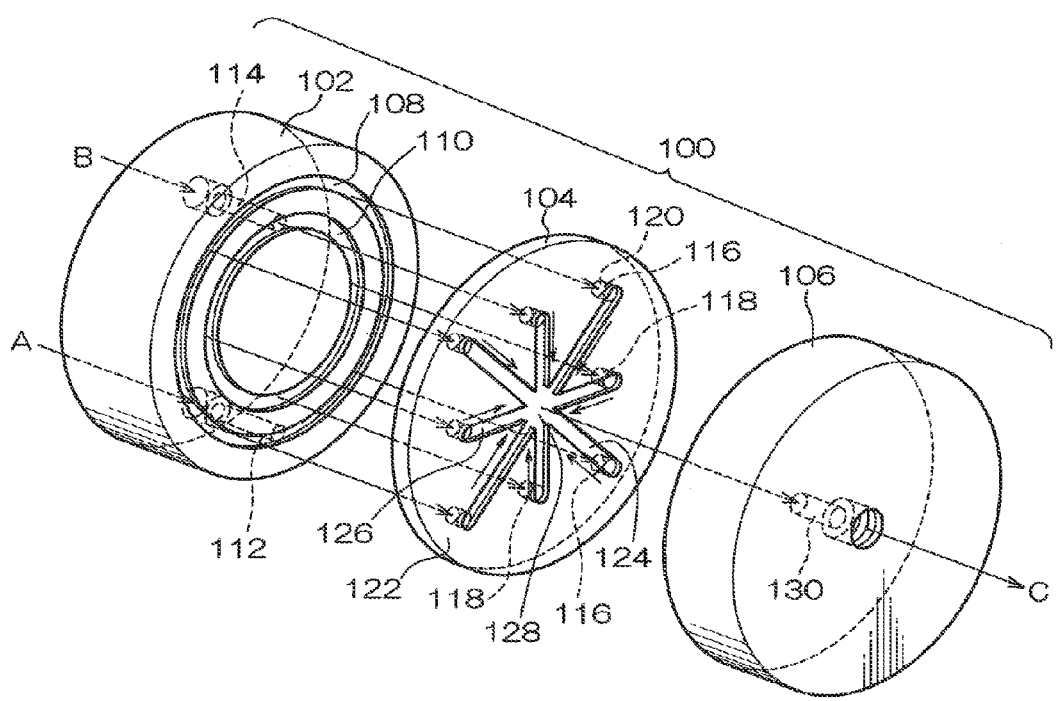
FIG. 1 is an exploded perspective view of a micro device as one example of a micro mixer.

The ceramide dispersion of the present invention is a ceramide dispersion which includes (1) ceramide-containing particles which contains a ceramide, which are dispersed in an aqueous phase as an oil-phase component and which have a volume average particle diameter from 1 nm to 100 nm and (2) a fatty acid component which is at least one of a fatty acid having a melting temperature not higher than 30° C. or a fatty acid salt; the amount of a nonionic surfactant being 0 or not more than 0.1 times the total mass of the ceramide; the amount of an ionic surfactant other than the fatty acid component being 0 or less than 0.05 times the total mass of the ceramide(s); and the pH being from 6 to 8.

Since the ceramide dispersion of the present invention contains the above-mentioned ceramide-containing particles and the above-mentioned fatty acid component and has a pH of from 6 to 8, even when the ceramide dispersion contains a surfactant other than the fatty acid components in an amount which is 0 or not more than 0.1 times the total mass of ceramide, the ceramide dispersion is a transparent ceramide dispersion, the ceramide-containing particles are stably dispersed, and the ceramide dispersion has a superior stability over time.

Accordingly, the present invention can provide a ceramide dispersion in which ceramide-containing particles having a very small particle diameter are stably dispersed and which has a superior stability over time.

The term "step" used herein includes not only a discrete step, but also steps which cannot be clearly distinguished from another step, as long as the expected effect of the pertinent step can be achieved.

In addition, ranges indicated herein with "to" include the numerical values before and after "to".

The invention will be described below.

The ceramide dispersion of the present invention is in a form of emulsion in which ceramide-containing particles which at least contain a ceramide are dispersed in an aqueous phase as an oil phase component. Here, the ceramide-containing particles as the oil phase component may be in a form of oil droplets in which the particles are completely dissolved, or in a form of partially insoluble solid as long as the diameter of the ceramide-containing particles is in a range prescribed in the present invention. Such oil droplets and solid are generally referred to herein as dispersed particles.

As the aqueous phase which constitutes a part of the ceramide dispersion of the present invention and which is a dispersion medium in which ceramide-containing particles are dispersed, an aqueous solution which contain as a main component an aqueous medium such as water may be used. Other than water, higher alcohols, or water-soluble functional components such as water-soluble antioxidants and plant extracts can be further added in an amount in which the effects of the present invention are not adversely affected.

In the following, a variety of components which are contained in the ceramide dispersion of the present invention will now be described.

(1) Ceramide-Containing Particles

The ceramide-containing particles of the present invention contain ceramide, are dispersed in an aqueous phase as an oil phase component, and have a volume average particle diameter from 1 nm to 100 nm.

The ceramide in the invention includes ceramide and derivatives thereof, which may be derived from a synthetic compound or an extracted product. The term "ceramide" as used herein includes a natural ceramide as described below, a compound having a natural ceramide as a basic skeleton, and a precursor which may be derived from these compounds, and is a collective name for a natural ceramide, a glycosylated ceramide such as a sphingoglycolipid, a synthetic ceramide, a sphingosine, a phytosphingosine, and derivatives thereof.

(Natural Ceramide)

The term "natural ceramide" as used herein means a ceramide which has the same structure as that present in the stratum corneum of human skin. A more preferred embodiment of the natural ceramide is that sphingoglycolipid is not contained and three or more hydroxyl groups are included in the molecular structure.

In the following, the natural ceramide used in the invention will be described in detail.

Examples of a fundamental structural formula of the natural ceramide which may be preferably used in the invention are shown in (1-1) to (1-10). (1-1) is known as ceramide 1, (1-2) is known as ceramide 9, (1-3) is known as ceramide 4, (1-4) is known as ceramide 2, (1-5) is known as ceramide 3, (1-6) is known as ceramide 5, (1-7) is known as ceramide 6, (1-8) is known as ceramide 7, (1-9) is known as ceramide 8, and (1-10) is known as ceramide 3B.

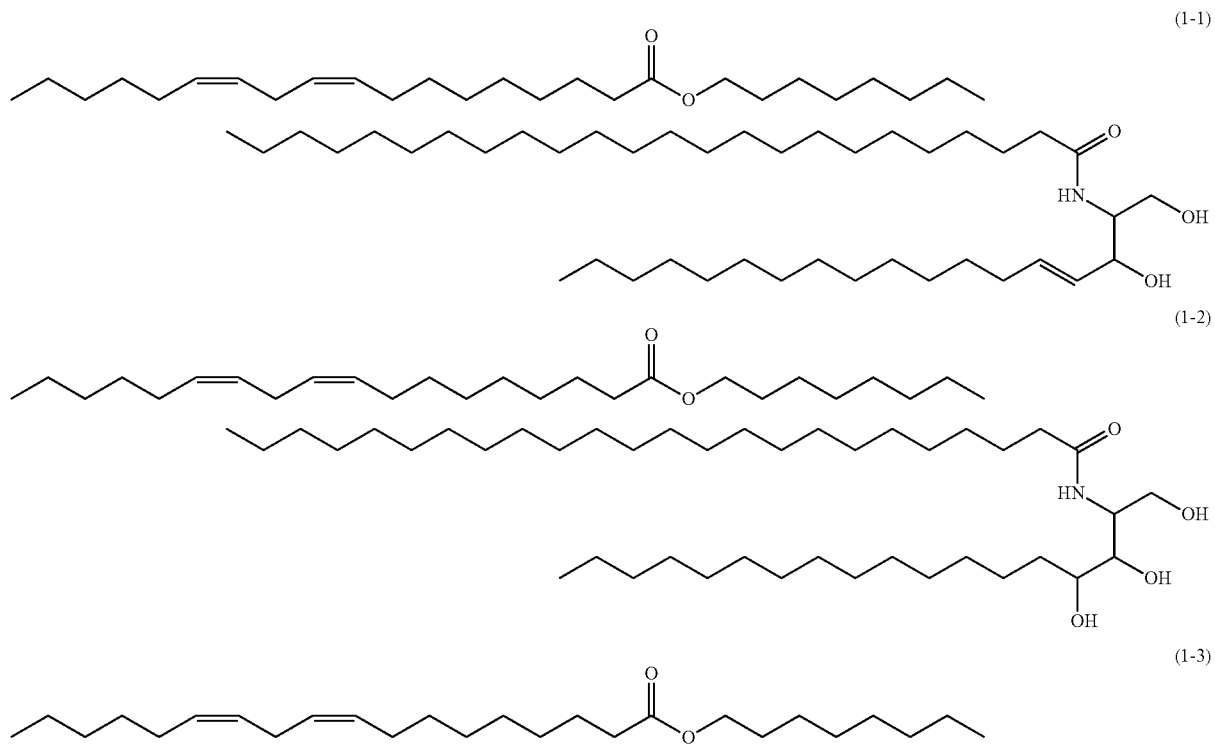

-continued
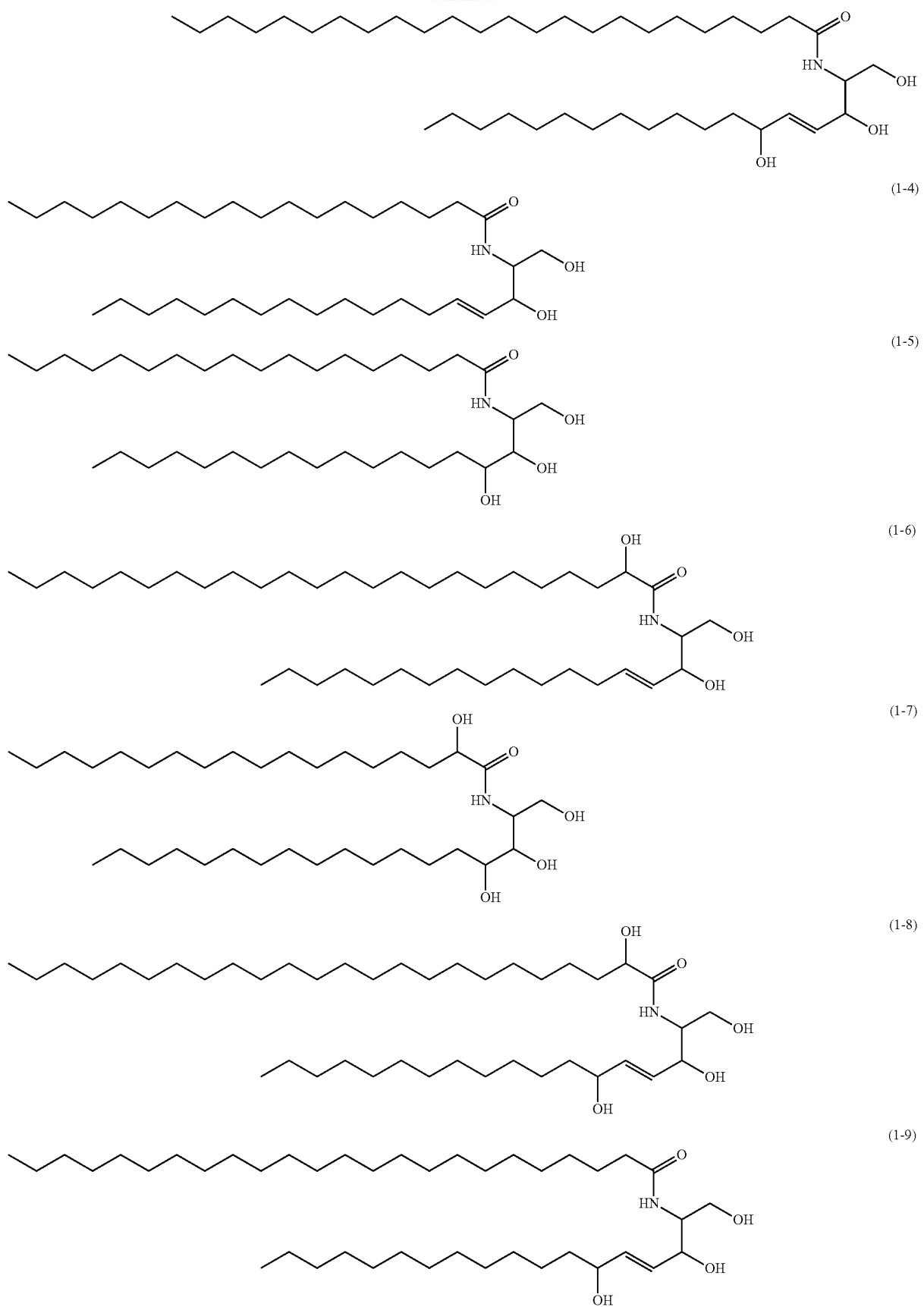
(1-4)
(1-5)
(1-6)
(1-7)
(1-8)
(1-9)

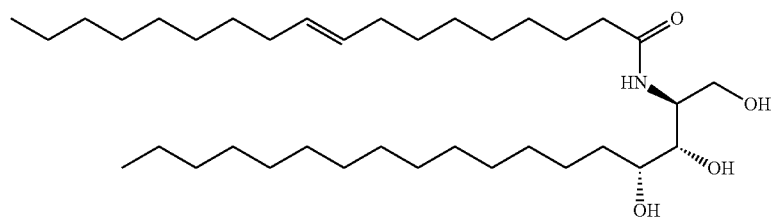

(1-10)

The above structural formula shows one example of each ceramide. Since ceramide is a natural substance, in ceramide actually derived from a human or an animal, there are various variation examples in the length of the alkyl chain, and ceramide having the above skeleton may have any structure in the alkyl chain length.

Alternatively, it is possible to use ceramide that have been modified according to purpose by, for example, introducing double bond(s) in the molecule to provide solubility for the purpose of, for example, incorporating into a formulation, or introducing hydrophobic group(s) to provide permeability.

Examples of the ceramide having a general structure, which referred to as the natural ceramide, include natural product (extract) and products obtained by microbial fermentation method. Further, synthetic substances and animal-derived substances may also be included.

A natural (D (−)) isomer) optically active substance is used as such ceramide. Furthermore, a non-natural (L (+)) isomer) optically active substance or a mixture of natural and unnatural type may be used, if necessary. A relative configuration of the above compounds may be natural configuration, or other non-natural configuration, or a mixture thereof.

Meanwhile, in the case of using a nanoceramide dispersion or composition for the purpose of, for example, a skin emollient, from the viewpoints of a barrier effect, it is preferable to use more of a natural optical isomer.

Such the natural ceramide are also available as a sold product, and examples include Ceramide I, Ceramide III, Ceramide IIIA ceramide IIIB, Ceramide IIIC, and Ceramide VI (all manufactured by Cosmofarm), Ceramide TIC-001 (manufactured by Takasago International Corporation), CERAMIDE II (manufactured by Quest International), DS-Ceramide VI, DS-CLA-Phytoceramide, C6-Phytoceramide, and DS-ceramide Y3S (manufactured by DOOSAN), and CERAMIDE2 (manufactured by Sedama), and the exemplified compound (1-5) is available as trade name: CERAMIDE 3, manufactured by Evonik (formerly Deggusa), and the exemplified compound (1-7) is available as trade name: CERAMIDE 6, manufactured by Evonik (formerly Deggusa).

The natural ceramide which is contained in the ceramide-containing particle may be used alone or in combination of two or more thereof. Generally, ceramide analogs have a high melting point and a high crystallinity. Therefore, the combination of two or more natural ceramide is preferable from the viewpoint of emulsion stability and handling performance.

(Glycosylated Ceramide)

The glycosylated ceramide is a ceramide compound containing saccharides in the molecule. Examples of the saccharides contained in the molecule of the ceramide compound include monosaccharides such as glucose or galactose; disaccharides such as lactose or maltose; and oligosaccharides and polysaccharides obtained by polymerizing these monosaccharides or disaccharides with a glycoside bond. Further, saccharides may be sugar derivatives in which a hydroxyl group in a sugar unit is replaced with other group. Examples of the sugar derivative include glucosamine, glucuronic acid, and N-acetyl glucosamine.

Among these, saccharides having 1 to 5 sugar units are preferable as the sugar unit in the molecule of the glycosylated ceramide from the viewpoint of dispersion stability. Specifically, glucose and lactose are preferable, and glucose is more preferable.

Specific examples of the glycosylated ceramide include the following compounds.

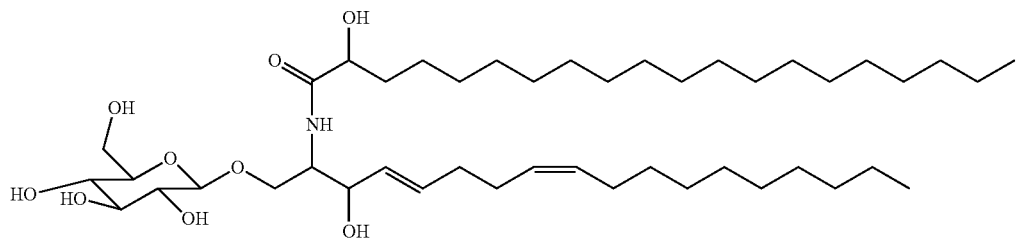

(4-1)

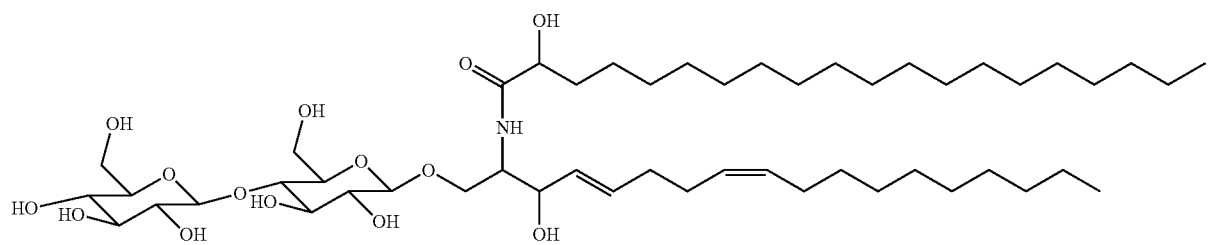

(4-2)

The glycosylated ceramide is available by synthesis or as a commercial product. For example, the exemplified compound (4-1) is available as a trade name: KOME SHINGOGLYCOLIPID manufactured by Okayasu Shoten Co., Ltd.

(Synthetic Ceramide)

The synthetic ceramide is synthesized in imitation of the structure of ceramide. As a known compound of such a synthetic ceramide, for example, the synthetic ceramide shown by the following structural formula may be used.

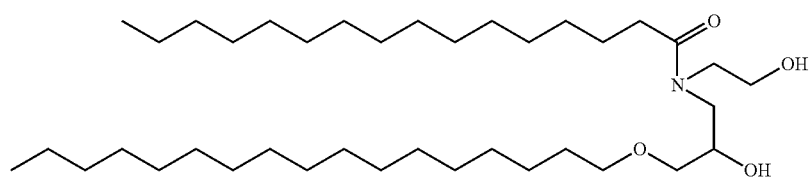 [SMILES: CCCCCCCCCCCCCCCCCOCC(O)CN(CCO)C(=O)CCCCCCCCCCCCCCC]

In the case of using the synthetic ceramide, for example, when the ceramide dispersion according to the present invention is used as a cosmetic product, from a viewpoint of an after-use feeling and a moisturizing feeling, a compound that is synthesized in imitation of the structure of the natural ceramide or the glycosylated ceramide are preferable, and a compound that is synthesized in imitation of the structure of the natural ceramide is more preferable.

(Sphingosine, Phytosphingosine)

For sphingosine and phytosphingosine, whether a synthetic product or a natural product, natural sphingosine or a sphingosine analog, or the combination thereof may be used.

Specific examples of the natural sphingosine include sphingosine, dihydrosphingosine, phytosphingosine, sphingadienine, dehydrosphingosine, dehydrophytosphingosine, and an N-alkylated body (e.g. N-methylated body) thereof, and an acetylated body thereof.

As these sphingosines, a natural (D (−) body) optically active body may be used, or a non-natural (L (+) body) optically active body may be used, or further, a mixture of a natural type and a non-natural type may be used. Relative configuration of the above compound may be natural configuration, may be other non-natural configuration, or may be configuration of a mixture thereof. Examples of phytosphingosine which may be preferably used in the invention include PHYTOSPHINGOSINE (INCI name; 8<sup>th</sup> Edition) and exemplified compounds described below.

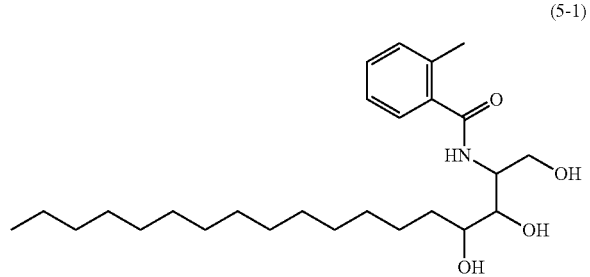

(5-1)

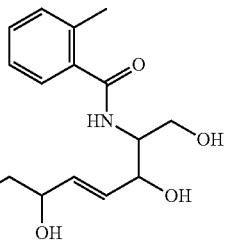

(5-2)

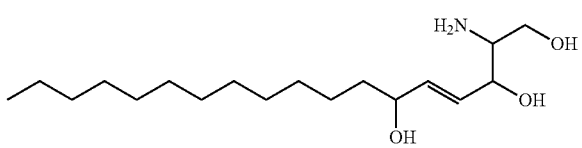

(5-3)

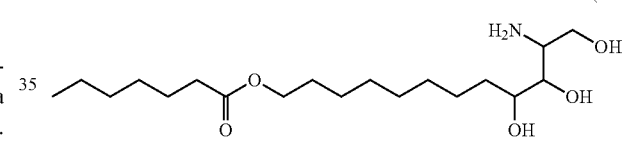

(5-4)

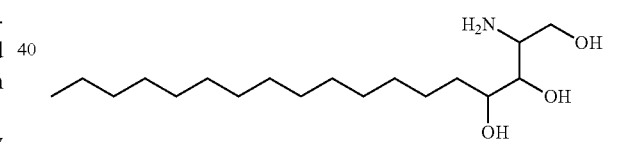

(5-5)

Phytosphingosine may be either a natural extract or a synthetic compound. It may be produced by synthesis or may be available as a commercial product.

Commercially available examples of the natural sphingosine include D-Sphingosine (4-Sphingenine) (manufactured by SIGMA-ALDRICH), D-Sphytosphingosine (manufactured by DOOSAN), phytosphingosine (manufactured by Cosmofarm). Further, Compound (5-5) as exemplified above is available as a trade name of "PHYTOSPHINGOSINE" (manufactured by Evonik (formerly Deggusa)).

Acid

When sphingosines such as sphingosine or phytosphingosine are used in the invention, they are preferably used in combination with a compound having an acidic residue capable of forming a salt with the sphingosines. Preferable examples of the compound having acidic residue include inorganic acids or organic acids having 5 or less carbon atoms.

Examples of the inorganic acid include phosphoric acid, hydrochloric acid, nitric acid, sulfuric acid, perchloric acid, and carbonic acid, and phosphoric acid and hydrochloric acid are preferable.

Examples of the organic acid include monocarboxylic acids such as formic acid, acetic acid, propionic acid, butyric acid, isobutyric acid, and valeric acid; dicarboxylic acids such as succinic acid, phthalic acid, fumaric acid, oxalic acid, malonic acid, and glutaric acid; oxycarboxylic acids such as glycolic acid, citric acid, lactic acid, pyruvic acid, malic acid, and tartaric acid; amino acids such as glutamic acid, and aspartic acid, and the like. As these compounds, phosphoric acid, hydrochloric acid, succinic acid, citric acid, lactic acid, glutamic acid, aspartic acid, or the combination thereof are preferable, and lactic acid, glutamic acid, aspartic acid or the combination thereof are particularly preferable.

The acid to be used together may be used by pre-mixing with sphingosines, may be added at the time of formation of the ceramide analogue containing particle, or may be added as a pH adjusting agent after the formation of the ceramide analogue containing particle.

When the acid is used together, the additive amount is preferably about 1 part by mass to 50 parts by mass relative to 100 parts by mass of sphingosines to be used.

—Ceramide Content—

In the ceramide dispersion of the present invention, it is preferred that ceramide-containing particles contain a ceramide in an amount of not less than 50% by mass with respect to the total mass of oil components contained in the oil phase, and, from the viewpoint of expecting that effective percutaneous or oral absorption of ceramide component and ceramide-induced effect be attained when the ceramide dispersion is applied to a variety of applications such as cosmetics, pharmaceuticals and foods, it is preferred that ceramide-containing particles contain a ceramide in an amount of from 50% by mass to 100% by mass, and more preferably, in an amount of from 75% by mass to 100% by mass. Thus, from the viewpoint of expecting that effects of natural ceramide be attained, it is preferred that natural ceramide be contained in an amount of not less than 50% by mass with respect to the total mass of ceramide contained in a high concentration in the ceramide dispersion, and most preferably in an amount of 100% by mass.

Here, in the ceramide dispersion of the present invention, the oil components contained in the oil phase represent, among the components contained in the oil phase, oil components having a physical property or functionality for application purposes of the ceramide dispersion, such as natural ceramide, the below mentioned ceramide analogues which may be used in combination therewith, as well as a variety of oil components including the below mentioned other oil components (e.g., fat-soluble carotenoids, fat-soluble vitamins, ubiquinones, fatty acids, oils and fats). It is noted that, among the components which may be used for preparing the oil phase, surfactants and water-soluble organic solvents are not included in the oil components of the present invention.

The content of ceramide in the ceramide dispersion is preferably in the range from 0.01% by mass to 5% by mass, and more preferably in the range from 0.1% by mass to 3% by mass. A ceramide dispersion containing a ceramide in the above mentioned range is preferred from the viewpoint of user's skin feel, for example, when the ceramide dispersion is applied to external preparations for skin such as cosmetics.

—Particle Diameter—

The ceramide-containing particles has a volume average particle diameter from 1 nm to 100 nm, preferably from 1 nm to 75 nm, more preferably from 1 nm to 50 nm, more preferably, and most preferably from 1 nm to 30 nm.

By making the particle diameter of ceramide-containing particle from 1 nm to 100 nm, transparency of the ceramide dispersion can be secured. When the ceramide dispersion of the present invention is used for, for example, cosmetics, pharmaceuticals or foods, the transparency of the composition is secured and desired effects such as skin absorbance can be favorably exerted.

The particle diameter of the ceramide-containing particle may be measured with a commercially available particle size distribution meter.

Known examples of the method for measuring particle size distribution include optical microscopy, a confocal laser scanning microscope method, an electron microscopic method, atomic force microscopy, a static light scattering method, laser diffractometry, dynamic light scattering, a centrifugal sedimentation method, electric pulse measurement, a chromatography method, and an ultrasonic attenuation method. Apparatuses based on each of these principles are commercially available.

In the measurement of the particle diameter of the ceramide-containing particle in the invention, it is preferable to use the dynamic light scattering from the viewpoint of particle diameter range and ease of measurement.

Examples of commercially available measuring apparatus using dynamic light scattering include a Nanotrac UPA (manufactured by Nikkiso Co., Ltd.), a dynamic light scattering particle size distribution meter LB-550 (manufactured by HORIBA Ltd.), and a concentrated-system particle diameter analyzer FPAR-1000 (manufactured by Otsuka Electronics Co., Ltd.).

The particle diameter of ceramide-containing particle in the invention is a value measured by using the dynamic light scattering particle size distribution meter LB-550 (manufactured by HORIBA Ltd.). Specifically, a value measured in the following manner is employed.

That is, in the method for measuring the particle diameter of the ceramide-containing particle, a sample divided from the ceramide dispersion of the invention is diluted with pure water so that the concentration of the oil component contained in the sample is 1% by mass and the particle diameter is measured using a quartz cell. The particle diameter may be determined as a median diameter when the refractive index of a sample is 1.600, the refractive index of a dispersion medium is 1.333 (pure water), and the viscosity of pure water is set as the viscosity of the dispersion medium.

Embodiments of the process of containing the ceramide-containing particles in the ceramide dispersion according to the present invention include: 1) a process of forming ceramide-containing particles (oil phase) in advance as solid particles and then dispersing these in a dispersion medium (aqueous phase); and 2) a process of forming a ceramide-containing particle in the system by heating ceramide analogs to change it into a molten state or dissolving a ceramide analog in an appropriate solvent to change it into a liquid state and then adding the resultant to the aqueous phase to disperse it, followed by reducing the temperature to ordinary ambient temperature or removing the solvent. Further, it is preferable that the natural ceramide or the like is prepared so as to be soluble in another oil component or is prepared by dissolving it in an organic solvent.

(Other Oil Components)

The ceramide dispersion of the invention is formed by dispersing a ceramide-containing particle in an aqueous phase as an oil phase. The ceramide dispersion may also have a configuration in which an oil component and/or solvent (may be referred to as "another (other) oil component(s)" in the present specification) different from the ceramide such as natural ceramide described above is contained in the oil phase, and an oil droplet-like dispersed particle containing natural ceramide is present as a natural ceramide-containing particle in the oil component and/or solvent. When this embodiment is used, the average particle diameter of the ceramide-containing particle in the invention means the average particle diameter of an oil droplet-like dispersed particle which contains a ceramide-containing particle.

In this regard, the term "another (other) oil component(s)" refers to an oil component which is not separated from the ceramide at an ordinary temperature. The term "solvent" refers to a solvent which may dissolve the ceramide, and examples thereof include alcohols.

Here, the other oil components usable in the present invention are not particularly limited. The other oil components may be components added as active component in accordance with the intended use of the ceramide dispersion, oil components used for improving dispersion stability or feeling with respect to skin or controlling the properties of a composition containing the ceramide dispersion. Hereinbelow, the other oil components usable in the present invention are described.

(Stenone, Sterol)

The ceramide dispersion according to the present invention may contain at least one of stenone and sterol as other oil components. These compounds are useful in improving the dispersion stability of the ceramide dispersion. Specific examples of stenones usable as the other oil components in the present invention include the following.

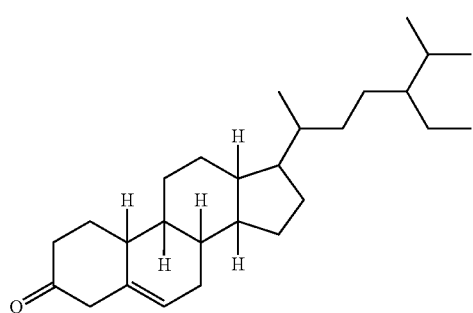

(2-1)

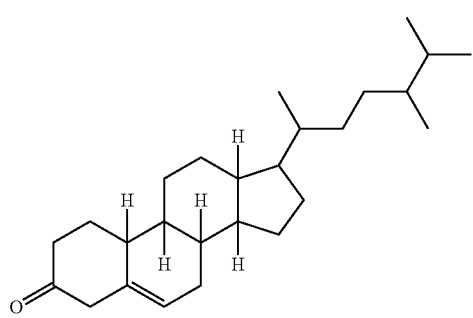

(2-2)

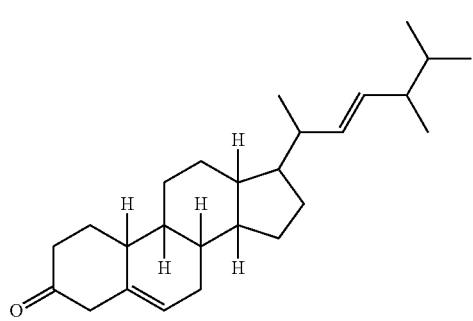

(2-3)

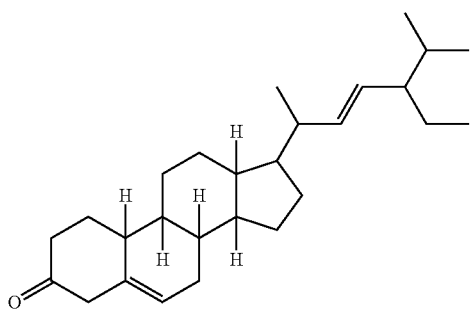

(2-4)

Specific examples of sterol include the following.

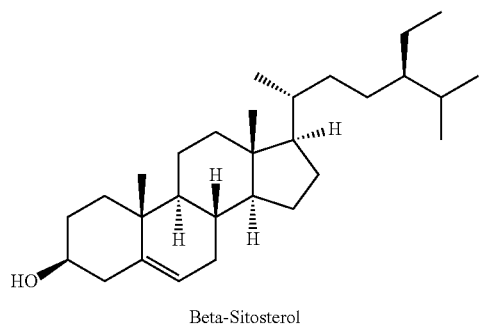

Beta-Sitosterol

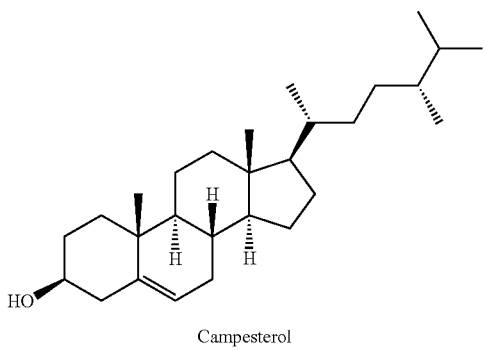

Campesterol

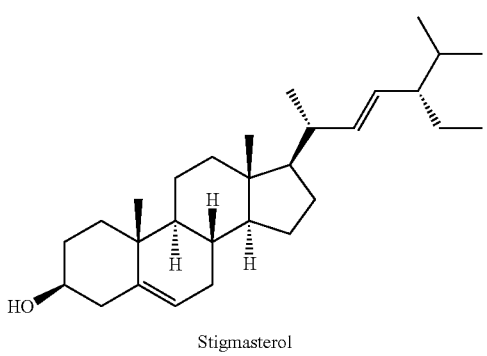

Stigmasterol

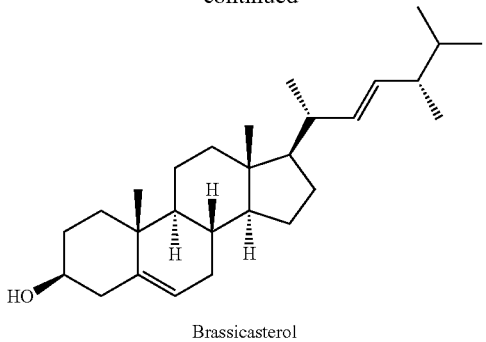

Brassicasterol

The stenone compound and the sterol compound can be obtained by synthesis or as a commercially available product.

For example, phytostenone can be obtained as UNIFETH (manufactured by Toyo Hakko Co., Ltd.) and PEO-sterol can be obtained from NIKKOL BPS-20 (manufactured by Nikko Chemicals Co., Ltd.).

Each of the stenone compound and the sterol compound may be used singly, or plural kinds thereof may be used.

In the case of using one stenone compound singly, from the viewpoints of the dispersion stability of the natural-ceramide-containing particles, the content of the stenone compound is preferably 50% by mass or less with respect to the total mass of the oil-phase components contained in the ceramide dispersion, and more preferably 30% by mass or less.

(Oil Component as an Active Component)

In the case of using the ceramide dispersion according to the present invention for the use of a cosmetic product or a pharmaceutical product, it is preferable to include a functional material for a cosmetic product or a pharmaceutical product that is insoluble or poorly soluble in a water-soluble medium, particularly in water, as an oil component.

The oil components usable in the present invention are not particularly limited as long as they are components that are soluble in an oil medium, and insoluble or poorly soluble in an aqueous medium, particularly, water. Preferable examples of the oil components include radical scavengers including carotenoid and an oil-soluble vitamin such as tocopherol, and a fat or oil, such as a coconut oil.

The term "insoluble in an aqueous medium" means that the solubility in 100 mL of an aqueous medium is 0.01 g or less at 25° C. The term "hardly-soluble in an aqueous medium means that the solubility in 100 mL of an aqueous medium is more than 0.01 g and 0.1 g or less at 25° C. The term "functional component" means a component which is expected to induce a certain physiological effect in a living body to which the functional component is applied.

Carotenoids

As the oil component, carotenoids including a natural colorant may be preferably used.

Carotenoids which may be used in the external composition of the invention are colorants of terpenoids ranging in color from yellow to red, and include natural substances such as plants, algae, and bacteria.

Further, carotenoids are not limited to naturally-derived substances. Any carotenoids are included in carotenoids in the invention as long as they are obtained according to the conventional method. For example, many of carotenes described later are also produced by synthesis, and many of commercially available β-carotenes are produced by synthesis.

Examples of the carotenoids include hydrocarbons (carotenes) and oxidized alcohol derivatives thereof (xanthophylls).

Examples carotenoids include actinioerythrol, bixin, canthaxanthin, capsanthin, capsorbin, β-8'-apo-carotenal (apocarotenal), β-12'-apo'-carotenal, α-carotene, β-carotene, "carotene" (mixtures of α- and β-carotenes), γ-carotene, β-cryptoxanthin, lutein, lycopene, violaxanthin, zeaxanthin, and esters of them which have a hydroxyl or carboxyl group.

Many of carotenoids exist in nature in the form of cis- and trans-isomers, and synthetic products are often cis-trans-mixtures.

Carotenoids may be generally extracted from plant materials. These carotenoids have various functions and, for example, lutein extracted from a petal of marigold is widely used as a raw material of a feed of poutly, and has the function of coloring a skin of poutly, and lipid, as well as an egg laid by poutly.

Fats or Oils

Examples of fats or oils used as other oil component include fats or oils which are liquid at a normal temperature (fatty oils) and fats or oils which are solid at a normal temperature (fats).

Examples of liquid fats or oils include an olive oil, a camellia oil, a macadamia nut oil, a castor oil, an avocado oil, an evening primrose oil, a turtle oil, a corn oil, a mink oil, a rapeseed oil, an egg yolk oil, a sesame oil, a persic oil, a wheat germ oil, a sasanqua oil, a flaxseed oil, safflower seed oil a cotton seed oil, a perilla oil, a soybean oil, an arachis oil, a tea seed oil, a kaya oil, a rice bran oil, a chinese wood oil, a Japanese tung oil, jojoba oil, a germ oil, a triglycerol, a glyceryl trioctanoate, a glycerin triisopalmitate, a salad oil, a safflower oil (*Carthamus tinctorius* oil), a palm oil, a coconut oil, a peanut oil, an almond oil, a hazelnut oil, a walnut oil, and a grape seed oil.

Examples of the solid fats or oils include a beef tallow, a hardened beef tallow, a neatsfoot oil, a beef bone fat, a mink oil, an egg yolk oil, a lard, a horse fat, a mutton tallow, a hardened oil, a cacao butter, a palm oil, a hardened palm oil, a palm oil, a palm hardened oil, a Japan wax, a Japan wax kernel oil, and a hardened castor oil.

Among them, a coconut oil which is a medium chain fatty acid triglyceride is preferably used from a viewpoint of the dispersed particle diameter and stability of the external composition.

In the invention, as the fats or oils, commercially available products may be used. Further, in the invention, the fats or oils may be used alone, or may be used by mixing them.

Examples of a compound having a phenolic hydroxyl group which may be used as other oil component in the invention include polyphenols (e.g. catechin), guaiac butter, nordihydroguaretic acid (NDGA), gallic acid esters, BHT (butylhydroxytoluene), BHA (butylhydroxyanisole), vitamin E group and bisphenols. Examples of gallic acid esters include propyl gallate, butyl gallate and octyl gallate.

Examples of the amine compound include phenylenediamine, diphenyl-p-phenylenediamine and 4-amino-p-diphenylamine, and diphenyl-p-phenylenediamine or 4-amino-p-diphenylamine is more preferable.

Examples of an oil-solubilized derivative of ascorbic acid or erythorbic acid include L-ascorbyl stearate, L-ascorbyl tetraisopalmitate, L-ascorbyl palmitate, erisorbyl palmitate, and erisorbyl tetraisopalmitate.

Among them, a vitamin E group is particularly preferably used from a viewpoint of excellence in safety and function of antioxidant.

The vitamin E group is not particularly limited. Examples of the vitamin E group include a compound group consisting of tocopherol and derivatives thereof, as well as a compound group consisting of tocotrienol and derivatives thereof. These may be used alone or in combination with a plurality of them. Alternatively, the compound selected from the group consisting of tocopherol and derivatives thereof may be used in combination with the compound selected from the group consisting of tocotrienol and derivatives thereof.

Examples of the compound group consisting of tocopherol and derivatives thereof include dl-α-tocopherol, dl-β-tocopherol, dl-γ-tocopherol, dl-δ-tocopherol, acetic acid dl-α-tocopherol, nicotinic acid-dl-α-tocopherol, linolic acid-dl-α-tocopherol, and succinic acid dl-α-tocopherol. Among them, dl-α-tocopherol, dl-β-tocopherol, dl-γ-tocopherol, dl-δ-tocopherol, and mixtures thereof (mixed tocopherol) are more preferable. As tocopherol derivatives, acetic esters of them are preferably used.

Examples of the compound group consisting of tocotrienol and derivatives thereof include α-tocotrienol, β-tocotrienol, γ-tocotrienol, and δ-tocotrienol. As tocotrienol derivatives, acetic esters thereof are preferably used. Tocotrienol is a tocopherol analog included in wheat, rice bran, and palm oil, has three double bonds in the side chain of tocopherol, and shows excellent antioxidant performance.

The vitamin E group are particularly preferably contained, in the oil phase of the ceramide dispersion as the oil-soluble antioxidant since the antioxidant function of the oil component may be effectively exhibited. Among the vitamin E group, at least one compound selected from the compound group consisting of tocotrienol and derivatives thereof is preferably contained from a viewpoint of the oxidation preventing effect.

In the ceramide dispersion of the present invention, the content of such other oil components used is preferably from 0.1% by mass to 50% by mass with respect to the total mass of the dispersion, more preferably from 0.2% by mass to 25% by mass, and still more preferably from 0.5% by mass to 10% by mass, from the viewpoint of dispersed particle diameter and emulsion stability, in view of application of, for example, pharmaceuticals and cosmetics.

When the content of the oil component is not less than 0.1% by mass as mentioned above, the ceramide dispersion can be easily applied to pharmaceuticals and cosmetics since the efficacy of the effective component can be sufficiently exerted. On the other hand, when the content of the oil component is not more than 50% by mass, increase in dispersed particle diameter and deterioration of emulsion stability are inhibited, whereby a stable composition is obtained.

(2) Fatty Acid Component

The fatty acid component of the present invention is at least one of a fatty acid having a melting point not higher than 30° C. or a fatty acid salt. Since such fatty acid components are easily dissolved in the process of mixing an oil phase component with an aqueous phase component, favorable dispersion stability can be obtained without impairing the transparency of a ceramide dispersion containing minute ceramide-containing particles.

In the present invention, the below-mentioned "surfactant" does not include this fatty acid component.

The fatty acid having a melting point not higher than 30° C. preferably maintains its liquid state at room temperature, and, from the viewpoint of stability at the time when the solvent is removed from the ceramide dispersion, examples thereof preferably include a fatty acid having a melting point from −60° C. to 25° C., and more preferably a fatty acid having a melting point from −60° C. to 20° C. As such a fatty acid, either a long chain saturated fatty acid or unsaturated fatty acid may be employed as long as the melting point is in the above mentioned range, and examples thereof may include C10-30 saturated or unsaturated fatty acids and combinations thereof. A fatty acid as a fatty acid component is included in the ceramide dispersion as an oil phase component.

The fatty acid salt, from the viewpoint of its solubility in the process of mixing an oil phase component with an aqueous phase component in the present invention, may be a fatty acid having any melting point, or may be a saturated fatty acid or an unsaturated fatty acid. Examples of the salt constituting the fatty acid salt include metallic salts such as sodium salts and potassium salts, basic amino acid salts such as L-arginine salts, L-histidine salts and L-lysine salts, alkanolamine salts such as triethanolamine salts, and combinations thereof. The type of salt may be selected according to the type of fatty acid used, and metallic salts such as sodium are preferred from the viewpoint of solubility and stability of dispersion liquid. Such fatty acid salts as fatty acid components may be employed as an aqueous phase component of the ceramide dispersion because these fatty acids may be dissolved in an aqueous medium.

Specific examples of the fatty acid component in the ceramide dispersion of the invention include fatty acids such as capric acid, lauric acid, myristic acid, palmitic acid, stearic acid, oleic acid, 12-hydroxy stearic acid, undecylenic acid, tolic acid, isostearic acid, arachidic acid, behenic acid, linolic acid, α-linolenic acid, γ-linolenic acid, arachidonic acid, docosahexaenoic acid (DHA), eicosapentaenoic acid (EPA), erucic acid, or the like and respective salts thereof. These components may be used alone or in combination of two or more thereof. From a viewpoint of color, smell, and skin irritation, the fatty acid component in the invention is preferably at least one kind selected from the group consisting of lauric acid, isostearic acid, oleic acid, γ-linolenic acid, α-linolenic acid, and respective salts thereof, particularly preferably oleic acid.

The amount of the fatty acid component contained in the ceramide dispersion of the invention is preferably the amount which may disperse the ceramide sufficiently. From a viewpoint of preservation stability and transparency of the ceramide dispersion, the amount is preferably from 0.01 to 1.0 times of the total mass of the ceramide. From a viewpoint of preservation stability, the amount is preferably from 0.05 to 0.5 times of the total mass of the ceramide. When the amount of the fatty acid component is 1.0 times or less of the total mass of the ceramide, it is preferable in that excessive separation or precipitation of fatty acid is suppressed. On the other hand, when the amount of the fatty acid component is 0.01 times or more of the total mass of the ceramide, it is preferable in that the fixation of the fatty acid component to the ceramide is sufficient.

From the viewpoint of transparency, it is preferred that the content of fatty acid components in the ceramide dispersion be from 0.01 to 1.0 times the total mass of ceramide. When the content of the fatty acid components is not less than 0.01 times the total mass of ceramide, the stability of the ceramide dispersion improves, but when the content of the fatty acid components is less than 0.01 times the total mass of ceramide, the ceramide cannot be sufficiently dispersed and is deposited. On the other hand, when the content of the fatty acid components is not more than 1.0 times the total mass of ceramide, the transparency of the ceramide dispersion can be attained and release of an excess amount of fatty acids can be inhibited. Therefore, the above range is preferable.

In order to obtain more favorable transparent ceramide, the content of fatty acid components in the ceramide dispersion is preferably from 0.01 times to 0.3 times the total mass of ceramide, and more preferably from 0.03 times to 0.2 times the total mass of ceramide. In order to obtain a ceramide dispersion having a more favorable preservation stability, the content of fatty acid components in the ceramide dispersion is preferably from 0.05 times to 0.5 times the total mass of ceramide, and more preferably from 0.03 times to 0.2 times the total mass of ceramide.

(3) Surfactant

The ceramide dispersion of the present invention contains nonionic surfactant in an amount of 0 or not more than 0.1 times the total mass of the ceramide, and the amount of ionic surfactant other than the fatty acid components in ceramide dispersion is in an amount of 0 or less than 0.05 times the total mass of the ceramide.

In the ceramide dispersion of the present invention, with the above-mentioned fatty acid components, the ceramide can be dispersed with good stability, and therefore, the amounts of nonionic surfactant and ionic surfactant other than the fatty acid components can be decreased as compared with the amounts which are usually employed. Here, "0 times the total mass of the ceramide" means that the ceramide dispersion does not contain surfactant other than fatty acid components.

Each of cationic, anionic and amphoteric surfactants is applicable to the ionic surfactant of the present invention, and preferable specific examples thereof include lecithins such as high purity lecithin, hydrogenated lecithin, enzymatically decomposed lecithin, enzymatically decomposed hydrogenated lecithin, hydroxy lecithin.

The amount of ionic surfactant added is less than 0.05 times the total mass of ceramide, and from the viewpoint of preservation stability of the ceramide dispersion, it is preferred that the amount be not more than 0.01 times the total mass of ceramide, and it is most preferred that the amount be 0, that is, the surfactants be not contained.

On the other hand, nonionic surfactants of the present invention may not be contained in the ceramide dispersion, and from the viewpoint of transparency and stability of ceramide dispersion liquid, nonionic surfactants may be contained in the ceramide dispersion in an amount not more than 0.1 times the total mass of ceramide.

Examples of the nonionic surfactant capable be contained in the ceramide dispersion include glycerole fatty acid ester, organic acid monoglyceride, polyglycerole fatty acid ester, propylene glycol fatty acid ester, polyglycerole condensed ricinoleic acid ester, sorbitan fatty acid ester, sucrose fatty acid ester, and polyoxyethylene sorbitan fatty acid ester. These may be used alone or two or more of these may be used in combination. These surfactants are not necessary to be a surfactant which is highly purified such as by distillation, and may be a reaction mixture. These nonionic surfactants can be contained as an oil phase component of the ceramide dispersion of the present invention.

Among the nonionic surfactants, polyglycerol fatty acid ester is preferable from a viewpoint of emulsion stability. Particularly, polyglycerol fatty acid ester with an HLB of form 10 to 16 (hereinafter, may be referred to as the "specific polyglycerol fatty acid ester") is more preferable. The polyglycerol fatty acid ester may be contained in the oil phase.

Surfactants such as the specific polyglycerole fatty acid ester is preferable since the specific polyglycerol fatty acid ester may reduce the interfacial tension of oil phase/aqueous phase greatly, and thereby the particle diameter of the ceramide-containing particle which is contained in the ceramide dispersion as an oil phase may be smaller.

Herein, HLB is hydrophilicity-hydrophobicity balance which is usually used in the field of surfactants, and a calculation equation which is usually used, for example, Kawakami equation may be used. In the invention, the following Kawakami equation is adopted.

$$HLB = 7 + 11.7 \log(M_w/M_o)$$

In the equation, $M_w$ is the molecular weight of a hydrophilic group, and $M_o$ is the molecular weight of a hydrophobic group.

Alternatively, numerical values of HLB described in catalogs may be used. As is apparent from the aforementioned equation, a surfactant of an arbitrary HLB value may be obtained by utilizing additivity of HLB.

As for the preferable examples of the polyglycerol fatty acid ester, it is particularly preferable that at least one of them is an ester of a polyglycerin with an average degree of polymerization of 10, and a fatty acid having 8 to 18 carbon atoms (for example, caprylic acid, capric acid, lauric acid, myristic acid, palmitic acid, stearic acid, oleic acid, and linolic acid).

Preferable examples of the polyglycerol fatty acid ester include hexaglycerol monooleate, hexaglycerol monopalmitate, hexaglycerol monomyristate, hexaglycerol monolaurate, decaglycerol monooleate, decaglycerol monostearate, decaglycerol monopalmitate, decaglycerol monomyristate, and decaglycerol monolaurate. The HLB values of these compounds are from 10 to 16.

Among them, decaglycerol monolinoleate (HLB=12), decaglycerol monooleate (HLB=12), decaglycerol monostearate (HLB=12), decaglycerol monopalmitate (HLB=13), decaglycerol monomyristate (HLB=14), decaglycerol monolaurate (HLB=16) or the like is more preferable. As the polyglycerol fatty acid ester, decaglycerol oleate is particularly preferable. In the invention, the specific polyglycerol fatty acid ester may be used alone or in combination of two or more thereof.

As for the surfactant in the invention, one selected from polyglycerol fatty acid ester with an HLB of from 10 to 16 and one or more selected from polyglycerol fatty acid ester with an HLB of from 5 to 15 which has a molecular structure different from the former polyglycerol fatty acid ester may be combined. In this regard, the polyglycerol fatty acid ester with an HLB of from 5 to 15 may be polyglycerol fatty acid ester which is contained in polyglycerol fatty acid esters as described above or may be other polyglycerol fatty acid esters.

In the invention, a preferred embodiment contains, as the surfactant, decaglycerol oleate and polyglycerol fatty acid ester in which the polymerization degree of glycerol is less than 10 and the number of carbon atom in fatty acid is from 12 to 18. A more preferable example of polyglyceryl fatty acid ester in which the degree of polymerization of the glycerol is less than 10 and the number of carbon atoms in fatty acid is from 12 to 18 includes polyglyceryl fatty acid ester which is at least one selected from hexaglycerol fatty acid ester and tetraglycerol fatty acid ester and has an HLB value of form 5.0 to 15.

Examples of hexaglycerol fatty acid ester and tetraglycerol fatty acid ester which are suitably used together with decaglycerol oleate include tetraglycerol monostearate (HLB=6), tetraglycerol monooleate (HLB=6), hexaglycerol monolaurate (HLB=14.5), hexaglycerol monomyristate (HLB=11), hexaglycerol monostearate (HLB=9), and hexaglycerol monooleate (HLB=9).

When decaglycerol oleate is used in combination with hexaglycerol fatty acid ester and/or tetraglycerol fatty acid ester in the invention, the content ratio may be properly determined according to the application form of the ceramide dispersion and (decaglycerol fatty acid ester)/(tetraglycerol fatty acid ester and/or hexaglycerol fatty acid ester) is preferably from 1/0 to 1/1, more preferably 1/0.5, and further preferably 1/0.25.

A commercially available product of polyglycerol fatty acid ester such as a specific polyglycerol fatty acid ester may be used.

Examples of the commercially available product of polyglycerol fatty acid ester include NIKKOL DGMS, NIKKOL DGMO-CV, NIKKOL DGMO-90V, NIKKOL DGDO, NIKKOL DGMIS, NIKKOL DGTIS, NIKKOL Tetraglyn 1-SV, NIKKOL Tetraglyn 1-O, NIKKOL Tetraglyn 3-S, NIKKOL Tetraglyn 5-S, NIKKOL Tetraglyn 5-O, NIKKOL Hexaglyn 1-L, NIKKOL Hexaglyn 1-M, NIKKOL Hexaglyn 1-SV, NIKKOL Hexaglyn 1-O, NIKKOL Hexaglyn 3-S, NIKKOL Hexaglyn 4-B, NIKKOL Hexaglyn 5-S, NIKKOL Hexaglyn 5-O, NIKKOL Hexaglyn PR-15, NIKKOL Decaglyn 1-L, NIKKOL Decaglyn 1-M, NIKKOL Decaglyn 1-SV, NIKKOL Decaglyn 1-50SV, NIKKOL Decaglyn 1-ISV, NIKKOL Decaglyn 1-O, and NIKKOL Decaglyn 1-OV, NIKKOL Decaglyn 1-LN, NIKKOL Decaglyn 2-SV, NIKKOL Decaglyn 2-ISV, NIKKOL Decaglyn 3-SV, NIKKOL Decaglyn 3-OV, NIKKOL Decaglyn 5-SV, NIKKOL Decaglyn 5-HS, NIKKOL Decaglyn 5-IS, NIKKOL Decaglyn 5-OV, NIKKOL Decaglyn 5-O-R, NIKKOL Decaglyn 7-S, NIKKOL Decaglyn 7-O and NIKKOL Decaglyn 10-SV, NIKKOL Decaglyn 10-IS, NIKKOL Decaglyn 10-OV, NIKKOL Decaglyn 10-MAC, and NIKKOL Decaglyn PR-20 (manufactured by Nikko Chemicals Co., Ltd.), Ryoto Polygly Ester, L-7D, L-10D, M-10D, P-8D, SWA-10D, SWA-15D, SWA-20D, S-24D, S-28D, O-15D, O-50D, B-70D, B-100D, ER-60D, LOP-120DP, DS13W, DS3, HS11, HS9, TS4, TS2, DL15, and DO13 (manufactured by Mitsubishi-Kagaku Foods Corporation); Sunsoft Q-17UL, Sunsoft Q-14S, and Sunsoft A-141C (manufactured by Taiyo Kagaku Co., Ltd.); and Poem DO-100 and Poem J-0021 (manufactured by Riken Vitamin Co., Ltd.).

Among them, NIKKOL Decaglyn 1-L, NIKKOL Decaglyn 1-M, NIKKOL Decaglyn 1-SV, NIKKOL Decaglyn 1-50SV, NIKKOL Decaglyn 1-ISV, NIKKOL Decaglyn 1-O, and NIKKOL Decaglyn 1-OV, NIKKOL Decaglyn 1-LN, Ryoto Polygly Ester, L-7D, L-10D, M-10D, P-8D, SWA-10D, SWA-15D, SWA-20D, S-24D, S-28D, O-15D, O-50D, B-70D, B-100D, ER-60D, and LOP-120DP are preferable.

As for sorbitan fatty acid ester which is another surfactant in the present invention, the number of carbon atoms in fatty acid is preferably 8 or more, more preferably 12 or more. Preferable examples of sorbitan fatty acid ester include sorbitan monocaprylate, sorbitan monolaurate, sorbitan monostearate, sorbitan sesquistearate, sorbitan tristearate, sorbitan isostearate, sorbitan sesquiisostearate, sorbitan oleate, sorbitan sesquioleate, and sorbitan trioleate.

In the invention, these sorbitan fatty acid esters may be used alone, or may be used by mixing them.

Examples of the commercially available product of sorbitan fatty acid ester include NIKKOL SL-10 and SP-10V, SS-10V, SS-10MV, SS-15V, SS-30V, SI-10RV, SI-15RV, S0-10V, SO-15MV, SO-15V, SO-30V, SO-10R, SO-15R, SO-30R, and SO-15EX (manufactured by Nikko Chemicals Co., Ltd.); Solgen 30V, 40V, 50V, 90, and 110 (manufactured by DAI-ICHI KOGYO SEIYAKU CO., LTD.); and RHEODOL AS-10V, AO-10V, AO-15V, SP-L10, SP-P10, SP-S10V, SP-S30V, SP-O10V, and SP-O30V (manufactured by Kao Corporation).

As for sucrose fatty acid ester, the number of carbon atom in fatty acid is preferably 12 or more, more preferably from 12 to 20.

Preferable examples of sucrose fatty acid ester include sucrose dioleate, sucrose distearate, sucrose dipalmitate, sucrose dimyristate, sucrose dilaurate, sucrose monooleate, sucrose monostearate, sucrose monopalmitate, sucrose monomyristate, and sucrose monolaurate. Among them, sucrose monooleate, sucrose monostearate, sucrose monopalmitate, sucrose monomyristate, and sucrose monolaurate are more preferable.

In the invention, these sucrose fatty acid esters may be used alone, or may be used by mixing them.

Examples of the commercial product of sucrose fatty acid ester include Ryoto sugar ester S-070, S-170, S-270, S-370, S-370F, S-570, S-770, S-970, S-1170, S-1170F, S-1570, S-1670, P-070, P-170, P-1570, P-1670, M-1695, O-170, O-1570, OWA-1570, L-195, L-595, L-1695, LWA-1570, B-370, B-370F, ER-190, ER-290, and POS-135 (manufactured by Mitsubishi-Kagaku Foods Corporation); and DK Ester SS, F160, F140, F110, F90, F70, F50, F-A50, F-20W, F-10, F-A10E, Cosmelike B-30, S-10, S-50, S-70, S-110, S-160, S-190, SA-10, SA-50, P-10, P-160, M-160, L-10, L-50, L-160, L-150A, L-160A, R-10, R-20, O-10, and O-150 (manufactured by DAI-ICHI KOGYO SEIYAKU CO., LTD.).

Among them, Ryoto sugar ester S-1170, S-1170F, S-1570, S-1670, P-1570, P-1670, M-1695, O-1570, L-1695, DK Ester SS, F160, F140, F110, Cosmelike S-110, S-160, S-190, P-160, M-160, L-160, L-150A, L-160A, and O-150 are preferable.

As for polyoxyethylene sorbitan fatty acid ester, the number of carbon atoms of fatty acid is preferably 8 or more, more preferably 12 or more. The length (the number of addition mole) of ethyleneoxide of polyoxyethylene is preferably 2 to 100, more preferably 4 to 50.

Preferable examples of polyoxyethylene sorbitan fatty acid ester include polyoxyethylene sorbitan monocaprylate, polyoxyethylene sorbitan monolaurate, polyoxyethylene sorbitan monostearate, polyoxyethylene sorbitan sesquistearate, polyoxyethylene sorbitan tristearate, polyoxyethylene sorbitan isostearate, polyoxyethylene sorbitan sesquiisostearate, polyoxyethylene sorbitan oleate, polyoxyethylene sorbitan sesquioleate, and polyoxyethylene sorbitan trioleate.

The polyoxyethylene sorbitan fatty acid esters may be used alone, or may be used by mixing them.

Examples of the commercially available product of polyoxyethylene sorbitan fatty acid ester include NIKKOL TL-10, NIKKOL TP-10V, NIKKOL TS-10V, NIKKOL TS-10MV, NIKKOL TS-106V, NIKKOL TS-30V, NIKKOL TI-10V, NIKKOL TO-10V, NIKKOL TO-10MV, NIKKOL TO-106V, and NIKKOL TO-30V (manufactured by Nikko Chemicals Co., Ltd.); RHEODOL TW-L106, TW-L120, TW-P120, TW-S106V, TW-S120V, TW-S320V, TW-O106V, TW-O120V, TW-O320V, TW-IS399C, RHEODOL SUPER SP-L10, and TW-L120 (manufactured by Kao Corporation); and SORGEN TW-20, TW-60V, and TW-80V (manufactured by DAI-ICHI KOGYO SEIYAKU CO., LTD.).

1-4. Polyhydric Alcohol

It is preferable that the ceramide dispersion of the invention contains polyhydric alcohol from a viewpoint of the particle diameter of the ceramide-containing particle, dispersion stability, preservation stability, and antiseptic properties.

The polyhydric alcohol has the moisturizing function and the viscosity adjusting function. In addition, the polyhydric alcohol also has the function of reducing the interface tension between water and a fat or oil component, making an interface easily spread, and making easier to form a fine and stable particle.

From the foregoing, inclusion of the polyhydric alcohol in the ceramide dispersion is preferable from a viewpoint that the dispersed particle diameter of the ceramide dispersion may be finer, and the particle diameter may be stably retained for a long period of time in the state where the particle diameter is fine.

In addition, by addition of the polyhydric alcohol, the moisture activity of the ceramide dispersion may be reduced, and proliferation of microorganisms may be suppressed.

The polyhydric alcohol which may be used in the invention is not particularly limited, as long as it is a di- or more hydric alcohol.

Examples of polyhydric alcohol include glycerin, diglycerin, triglycerin, polyglycerin, 3-methyl-1,3-butanediol, 1,3-butylene glycol, isoprene glycol, polyethylene glycol, 1,2-pentanediol, 1,2-hexandiol, propylene glycol, dipropylene glycol, polypropylene glycol, ethylene glycol, diethylene glycol, pentaerythritol, neopentyl glycol, maltitol, reduced starch syrup, saccharose, lactitol, palatinit, erythritol, sorbitol, mannitol, xylitol, xylose, glucose, lactose, mannose, maltose, galactose, fructose, inositol, pentaerythritol, maltotriose, sorbitan, trehalose, amylolysis sugar, and amylolysis sugar reduced alcohol. These compounds may be used alone, or in the form of a mixture of plural kinds.

It is preferred that polyhydric alcohol in which the number of hydroxyl groups in one molecule is three or more be used. By this, the interfacial tension between an aqueous solvent and oils or fats components can be lowered more effectively, and more minute and stable particulates can be formed. As the result, in the ceramide dispersion, a higher intestinal absorption can be attained when the ceramide dispersion is used for foods, and a higher skin absorption can be attained when the ceramide dispersion is used for percutaneous pharmaceuticals or cosmetics.

Among polyhydric alcohols satisfying the aforementioned conditions, particularly when glycerin is used, the particle diameter of the dispersed particle in the ceramide dispersion becomes more smaller, and the particle is stably retained for a long period of time while the particle diameter is small, being preferable.

From the viewpoint of the above-mentioned particle diameter, stability, antisepsis as well as viscosity of the ceramide dispersion and composition, the content of polyhydric alcohol is preferably from 5 to 60% by mass, and more preferably from 10 to 55% by mass, and still more preferably from 30 to 50% by mass with respect to the total mass of the ceramide dispersion.

When the content of the polyhydric alcohol is not less than 5% by mass, sufficient preservation stability is obtained easily irrespective of the kind of fat or oil component or the amount thereof, which is preferable. On the other hand, when the content of polyhydric alcohol is not more than 60% by mass, maximum effect is obtained and it is easy to prevent the viscosity of the ceramide dispersion from increasing, which is preferable.

(5) Good Solvent for Ceramides

The ceramide dispersion of the present invention may further contain a good solvent for ceramides. Such good solvent is not included in "an oil component" herein.

Examples of good solvent for ceramides include a solvent in which at least 0.1% or more by mass of ceramides can be dissolved at a temperature of 25° C. and which is liquid at room temperature. In the present invention, good solvent may be any substance as long as it is oil or fat or solvent in which not less than 0.1% by mass of ceramides can be dissolved.

The good solvent of the present invention is preferably a water-soluble organic solvent.

The water-soluble organic solvent of the present invention is used as an oil phase containing natural components when mixed with aqueous solution as an aqueous phase of the present invention. This aqueous organic solvent is at the same time a main component of extracting liquid which extracts natural components. That is, in the present invention, the natural components may be used for mixing with an aqueous solution in a state in which the natural components are extracted into an extracting liquid containing water-soluble organic solvent as a main component.

The term "water-soluble organic solvent" to be used in the invention means an organic solvent whose solubility to water (at 25° C.) is 10% by mass or more. The solubility to water is preferably 30% by mass or more, further preferably 50% by mass or more from the viewpoint of the stability of the produced dispersion.

The water-soluble organic solvent may be used alone or a mixture solvent of a plurality of the water-soluble organic solvents may be used. Further, it may be used as a mixed with water. When the mixture with water is used, the content of the water-soluble organic solvent is preferably 50% by volume or more, more preferably 70% by volume or more.

The water-soluble organic solvent is preferably used to mix the oil phase component to prepare the oil phase in the method for producing the ceramide dispersion to de described later. It is preferable that the water-soluble organic solvent is removed after it is mixed with the aqueous phase.

Examples of the water-soluble organic solvent include methanol, ethanol, 1-propanol 2-propanol, 2-butanol, acetone, tetrahydrofuran, acetonitrile, methyl ethyl ketone, dipropylene glycol monomethyl ether, methyl acetate, methyl acetoacetate, N-methylpyrrolidone, dimethylsulfoxide, ethylene glycol, 1,3-butanediol, 1,4-butanediol, propylene glycol, diethylene glycol, triethylene glycol, and mixtures thereof. Among them, ethanol, propylene glycol or acetone is preferable and ethanol or a mixed solution of ethanol and water is particularly preferable when their applications are limited to food products.

(6) Other Components

In accordance with the application of the ceramide dispersion of the present invention, other additives such as a variety of medicinal ingredient, antiseptics, coloring agents which are usually used for their applications may be combined with the ceramide dispersion of the present invention as long as the additives do not impair the effects of the present invention.

When the ceramide dispersion is used for a composition for external use such as an external preparation for skin, examples of the other components include a moisturizing agent such as glycine betaine, xylitol, trehalose, urea, neutral amino acid and basic amino acid; a drug efficacy agent such as allantoin; an organic powder such as cellulose powder, nylon powder, crosslinked silicone powder, crosslinked methylpolysiloxane, porous cellulose powder and porous nylon powder; an inorganic powder such as anhydrous silica, zinc oxide, and titanium oxide; a refreshing agent such as menthol and camphor, a plant extract, a pH buffer, an antioxidant, an ultraviolet absorbing agent, an ultraviolet scattering agent, an antiseptic, a perfume, a fungicide, and a coloring matter.

In the ceramide dispersion of the invention, when a ceramide-containing particle is used for the oil phase together with another oil component, the particle diameter of the dispersed particle contained as the oil phase may be made smaller by factors such as stirring conditions (shearing force, temperature, or pressure) in the method for producing the ceramide dispersion described below, conditions of use of the micro mixer, or the ratio of the oil phase to the aqueous phase, in addition to factors caused by the components contained in the ceramide dispersion, so that fine-grained oil-phase particles with a particle diameter of 100 nm or less may be obtained.

The transparency of the ceramide dispersion of the invention may be roughly determined by visually confirming the appearance. Generally, it may be determined by the turbidity of the ceramide dispersion. The turbidity of the ceramide dispersion may be measured as an absorbance of 660 nm at 25° C. in a cell of 10 mm using UV-VIBLE spectral photometer UV-2550 (manufactured by Shimadzu Corporation). When the turbidity of the ceramide dispersion of the invention is measured using an absorbance of 660 nm and the value is 0.050 or less, the ceramide dispersion is evaluated as a transparent ceramide dispersion of the present invention. The transparency of the ceramide dispersion is preferably 0.040 or less.

The pH of the ceramide dispersion of the invention is preferably from 6 to 8, more preferably from 7 or more to less than 8. When the pH of the ceramide dispersion is within the range, the ceramide dispersion having good dispersion stability and preservation stability is obtained. Various pH regulating agents may be used in order to adjust the pH of the ceramide dispersion to the range.

The pH regulating agent may be added or blended so as to have a pH within a predetermined range of pH values of the ceramide dispersion when the oil phase or aqueous phase is prepared or may be directly added to the obtained ceramide dispersion. Usable examples of the pH regulating agent include an acid such as hydrochloric acid or phosphoric acid; an alkali such as sodium hydroxide; various inorganic salts that are generally used in the field; and a buffer such as lactic acid-sodium lactate, citric acid-sodium citrate and succinic acid-sodium succinate.

<Method for Producing Ceramide Dispersion>

The ceramide dispersion of the present invention is a transparent ceramide dispersion which includes ceramide-containing particles which are dispersed in an aqueous phase as an oil-phase component and a fatty acid component which is an oil phase component or an aqueous phase component, in which the amount of surfactant is small or surfactant is not contained and the pH is from 6 to 8; and the ceramide dispersion of the present invention is obtained by a production method, the method including mixing an oil phase component containing at least the ceramide with an aqueous phase component at a temperature not higher than 40° C.

According to the method, the oil phase component and the aqueous phase component are mixed at 40° C. or less, whereby the oil phase component is well dissolved and a ceramide dispersion having excellent temporal stability and preservation stability may be obtained.

When the oil phase is prepared, it is preferable to use a water-soluble organic solvent mentioned above in order to dissolve the ceramide. Examples of the water-soluble organic solvent to be used for this purpose may include the above described examples.

In the mixing of the aqueous phase component and the oil phase component, known methods such as a high-pressure emulsification method that applies a shearing force of 100 MPa or more or a jet injection method that directly injects the oil phase component into the aqueous phase component may be used. It is preferable to apply a method using a micro mixer in which the oil phase component and the aqueous phase component are independently passed through a micro path in which the cross-section area of the narrowest portion is 1 $\mu m^2$ to 1 $mm^2$, and then respective phases are mixed from a viewpoint of the particle diameter of the ceramide-containing particle, the dispersion stability, and the preservation stability.

In the mixing, it is preferable that the viscosity of the aqueous phase is 30 mPa·s or less from a viewpoint of finely-dividing of the ceramide-containing particle.

In the present invention, the temperature at the time when the oil phase components and the aqueous phase components are mixed is not higher than 40° C. The temperature of not higher than 40° C. is attained when the oil phase components and the aqueous phase components are mixed, and the set temperature range may be changed as required according to a mixing (emulsifying) method which is applied. In a method using a micromixer, at least a temperature in the range before mixing and immediately after mixing is not higher than 40° C. For example, the temperature is determined based on each of the temperatures of the aqueous phase components and the oil phase components just before mixing and the temperature measured immediately after dispersion. From the viewpoint of stability of the ceramides dispersion over time, it is preferred that the temperature of the dispersion during mixing be not higher than 35° C.

Examples of the method for producing the ceramide dispersion of the present invention includes: a) preparing an aqueous phase using the aqueous medium (water etc.) containing a fatty acid salt (when it is existent); b) preparing an oil phase using the oil phase component which includes at least a ceramide; and c) mixing and dispersing the oil phase and the aqueous phase by the method described later, using the micro mixer to produce a ceramide dispersion (emulsion) which contains a ceramide-containing particle (a dispersed particle) having a volume average particle diameter of from 1 nm to 100 nm.

The ratio (mass) of the oil phase and the aqueous phase in the emulsification dispersion is not particularly limited. The oil phase/aqueous phase ratio (mass %) is preferably from 0.1/99.9 to 50/50, more preferably from 0.5/99.5 to 30/70, further preferably from 1/99 to 20/80.

When the oil phase/aqueous phase ratio is within the above range, it is preferable in that an active component is sufficiently contained, and practically sufficient emulsion stability is obtained.

When a composition in powder form is produced using the ceramide dispersion, the composition in powder form may be obtained by adding the process of drying the ceramide dispersion in emulsion form by spray drying and the like.

In the method for producing the ceramide dispersion, the components contained in the oil phase and the aqueous phase is the same as the components of the ceramide dispersion of the invention, and a preferable example and an addition amount thereof are the same as those of the ceramide dispersion, and the preferable combination of the components is also the same.

(Micro Mixer)

In the production method to be applied to the production of the ceramide dispersion of the present invention, it is preferable to take a method of passing the oil phase component and the aqueous phase component each independently through a micro path in which the cross-section area of the narrowest portion is from 1 $\mu m^2$ to 1 $mm^2$, and combining and mixing respective components in order to stably form a natural ceramide-containing particle having a particle diameter of from 1 nm to 100 nm.

The mixing of the oil phase component and the aqueous phase component is preferably mixing by countercurrent collision from a viewpoint of obtaining the finer dispersed particle.

The most suitable device for mixing by countercurrent collision is a countercurrent collision-type micro mixer. The micro mixer mixes mainly two different liquids in a fine space, one of liquids is an organic solvent phase containing a functional oil component, and the other is an aqueous phase which is an aqueous solution.

When the micro mixer is applied to preparation of an emulsion having the small particle diameter which is one of microchemistry processes, a good emulsion or dispersion having relatively low energy and small heat production, having the more uniform particle diameter as compared with a normal stirring emulsification dispersing system or high pressure homogenizer emulsification dispersing, and also having the excellent storage stability is easily obtained. This is an optimal method for emulsifying a natural component which is easily thermally degraded.

A summary of a method of emulsification or dispersing using the micro mixer include dividing the aqueous phase and the oil phase into fine spaces, respectively, and contacting or colliding respective fine spaces. This method is clearly different from a membrane emulsification method or a micro channel emulsification method which is a method in which only one is divided into a fine space, and the other is a bulk and, even when only one is actually divided into a fine space, the effect as in the invention is not obtained. As the known micro mixer, there are a variety of structures. When attention is paid to flow and mixing in a micro path, there are two kinds of a method of mixing while a laminar flow is maintained, and a method of mixing while disturbed, that is, in a disturbed flow. In the method of mixing while a laminar flow is maintained, mixing is effectively performed by making a size of a path depth greater than a path width, thereby, increasing the area of an interface between two liquids as much as possible, and making thicknesses of both layers smaller. Alternatively, a method of adopting a multilayer flow by dividing an entrance for two liquids into many potions, and flowing two liquids alternately has been also devised.

On the other hand, in a method of mixing with the disturbed flow, a method of flowing respective flows at a relatively high speed by dividing them into narrow paths is general. A method of ejecting one of fluids into the other liquid introduced into a fine space using an arrayed micro-nozzle has been also proposed. Alternatively, a method of forcibly contacting liquids flowing at a high speed using various means is good, particularly in the mixing effect. In the former method using a laminar flow, generally, a produced particle is large, and distribution is relatively uniform, on the other hand in the latter method using a disturbed flow, there is a possibility that a very fine emulsion is obtained. In respect of stability and transparency, the method using a disturbed flow is preferable in many cases. As the method using a disturbed flow, a comb tooth type and a collision type are representative. The comb tooth type micro mixer has a structure in which two comb tooth-like paths are faced, and arranged so that one path enters between two the other paths, alternately a representative of which is a mixer manufactured by IMM.

The collision-type micro mixer, represented by a KM mixer, has a structure in which forcible contact is tried utilizing the kinetic energy. Specifically, there is a central collision-type micro mixer disclosed by Nagasawa et al. ("H. Nagasawa et al., Chem. Eng. Technol., 28, No. 3, 324-330 (2005)", JP-A No. 2005-288254). In the method of countercurrently colliding an aqueous phase and an organic solvent phase, since a mixing time is extremely short, and an oil phase droplet is instantly formed, an extremely fine emulsion or dispersion is easily formed.

In the invention, when emulsification is performed by micro-mixing with the collision-type micro mixer, a temperature at emulsification (emulsification temperature) is such that micro-mixing is performed at a temperature of the aforementioned separate fine space of the micro mixer (temperature at micro-mixing part of micro mixer) at preferably 40° C. or lower, more preferably 0° C. to 40° C., particularly preferably 5° C. to 30° C., from a viewpoint of particle diameter uniformity of the resulting emulsion. By adopting the emulsification temperature of 0° C. or higher, since a main component of a dispersing medium is water, the emulsification temperature may be managed, being preferable. A retained temperature of the fine space of the micromixer is preferably 40° C. or lower. By adopting the retained temperature of 40° C. or lower, management of the retained temperature may be easily controlled, and the micro-bumping phenomenon which adversely influences on emulsification performance may be excluded. It is further preferable that the retained temperature is controlled at a temperature of 35° C. or lower.

In the invention, it is particularly preferable that retained temperatures of the aqueous phase and the oil phase before and after division into the fine space of the micro mixer, and of the fine space of the micro mixer and the separate fine space are higher than room temperature and, after micro-mixing and emulsification, an oil-in-water emulsion obtained with the micro mixer is cooled to a normal temperature after collection.

The cross-sectional area of a narrowest part of the fine space (path) of the micro mixer in the invention is 1 $\mu m^2$ to 1 $mm^2$ and, from a viewpoint of reducing the emulsion particle diameter and sharpness of the particle diameter distribution, preferably 500 $\mu m^2$ to 50,000 $\mu m^2$.

The cross-sectional area of a narrowest part of the fine space (path) of the micro mixer used in the aqueous phase in the invention is particularly preferably 1,000 $\mu m^2$ to 50,000 $\mu m^2$ from a viewpoint of mixing stability.

The cross-sectional area of a narrowest portion of the fine space (path) of the micro mixer used in the oil phase is particularly preferably 500 $\mu m^2$ to 20,000 $\mu m^2$ from a viewpoint of reducing of the emulsion particle diameter and sharpness of the particle diameter distribution.

When emulsification and dispersing are performed with the micro mixer, the flow rate of the oil phase and the aqueous phase at emulsification and dispersing are different depending on the micro mixer used and, from a viewpoint of reducing of the emulsion particle diameter and sharpness of the particle diameter distribution, the flow rate of the aqueous phase is preferably 10 ml/min to 500 ml/min, more preferably 20 ml/min to 350 ml/min, particularly preferably 50 ml/min to 200 ml/min.

The flow rate of the oil phase, from a viewpoint of reducing of the emulsion particle diameter and sharpness of the particle diameter distribution, is preferably 1 ml/min to 100 ml/min, more preferably 3 ml/min to 50 ml/min, particularly preferably 5 ml/min to 50 ml/min.

The value obtained by dividing flow rates of both phases by the cross-sectional area of a micro channel, that is, the flow speed ratio (Vo/Vw) of both phases is preferably in the range from 0.05 to 5 from a viewpoint of miniaturization of a particle and design of the micromixer, wherein Vo is the flow speed of an organic solvent phase containing a water-insoluble natural component, and Vw is the flow speed of an aqueous phase. And, the flow speed ratio (Vo/Vw) from 0.1 to 3 is the most preferable range from a viewpoint of further miniaturization of a particle.

In addition, liquid sending pressures of the aqueous phase and the oil phase are preferably 0.030 MPa to 5 MPa and 0.010 MPa to 1 MPa, more preferably 0.1 MPa to 2 MPa and 0.02 MPa to 0.5 MPa, particularly preferably 0.2 MPa to 1 MPa and 0.04 MPa to 0.2 MPa, respectively. By adopting the liquid sending pressure of the aqueous phase of 0.030 MPa to 5 MPa, it is preferable in that the stable solution sending flow rate tends to be maintained. By adopting the liquid sending pressure of the oil phase of 0.010 MPa to 1 MPa, it is preferable in that the uniform mixing property tends to be obtained.

In the invention, the flow rate, the solution sending pressure and the retained temperature are more preferably a combination of respective preferably examples.

Then, a route from introduction of the aqueous phase and the oil phase into the micro mixer to discharge as an O/W emulsion will be explained using an example of a micro device (FIG. 1) as one example of the micro mixer in the invention.

As shown in FIG. 1, a micro device 100 is constructed of a supply element 102, a confluence element 104 and a discharge element 106, each in a cylindrical form.

On a surface opposite to the confluence element 104 of the supply element 102, a cross-section as a path for the oil phase or the aqueous phase in the invention is such that rectangular annular channels 108 and 110 are concentrically formed. In the supply element 102, bores 112 and 114 leading to each annular channel are formed, penetrating in a direction of its thickness (or height) direction.

In the confluence element 104, a bore 116 penetrating in its thickness direction is formed. In this bore 116, when an element is secured thereto in order to construct the micro device 100, an end 120 of the bore 116 situated on a surface of the confluence element 104 opposite to the supply element 102 is opened in the annular channel 108. In an embodiment shown, four bores 116 are formed, and they are arranged at an equal interval in a circumferential direction of the annular channel 108.

In the confluence element 104, a bore 118 is formed, penetrating therethrough, like the bore 116. The bore 118 is formed so as to be opened in the annular channel 110, like the bore 116. Bores 118 are arranged at an equal interval in a circumferential direction of the annular channel 110, and the bore 116 and the bore 118 are arranged so as to be positioned alternately.

On a surface 122 opposite to the discharge element 106 of the confluent element 104, the micro channels 124 and 126 are formed. One end of this micro channel 124 or 126 is an opening part of the bore 116 or 118, the other end is a center 128 of the surface 122, and all micro channels extend from bores towards this center 128, and are converged at a center. A cross-section of the micro channel may be, for example, rectangular.

In the discharge element 106, a bore 130 passing a center thereof and penetrating in a thickness direction is formed. Therefore, this bore is opened in the center 128 of the confluence element 104 at one end, and is opened in the outside of the micro device at the other end.

In the present micro device 100, fluids A and B supplied from the outside of the micro device 100 at ends of bores 112 and 114 are flown into annular channels 108 and 110 via bores 112 and 114, respectively.

The annular channel 108 and the bore 116 are communicated, and the fluid A which has flown into the annular channel 108 enters a micro channel 124 via the bore 116. In addition, the annular channel 110 and the bore 118 are communicated, and the fluid B which has flown into the annular channel 110 enters a micro channel 126 via the bore 118. Fluids A and B are flown into micro channels 124 and 126, respectively, and are flown towards a center 128, and are converged.

The converged fluids are discharged as a stream C to the outside of the micro device via the bore 130.

Such the micro device 100 may have the following specifications.

Cross-sectional shape of annular channel 108/width/depth/diameter: rectangle/1.5 mm/1.5 mm/25 mm Cross-sectional shape of annular channel 110/width/depth/diameter: rectangle/1.5 mm/1.5 mm/20 mm Diameter and length of bore 112: 1.5 mm/10 mm (circular cross-section)

Diameter and length of bore 114: 1.5 mm/10 mm (circular cross-section)

Diameter and length of bore 116: 0.5 mm/4 mm (circular cross-section)

Diameter and length of bore 118: 0.5 mm/4 mm (circular cross-section)

Cross-sectional shape of micro channel 124/width/depth/length/cross-sectional area: rectangle/350 μm/100 μm/12.5 mm/35000 μm$^2$ Cross-sectional shape of micro channel 126/width/depth/length/cross-sectional area: rectangle/50 μm/100 μm/10 mm/5000 μm$^2$ Diameter and length of bore 130: 500 μm/10 mm (circular cross-section)

The size of the micro channel (in FIGS. 1, 124 and 126) in which the aqueous phase and the oil phase are collided is defined in the preferable range in context with flow rates of the aqueous phase and the oil phase.

In the invention, the micro mixer disclose in JP-A No. 2004-33901 may be also preferably used.

Figure 2:
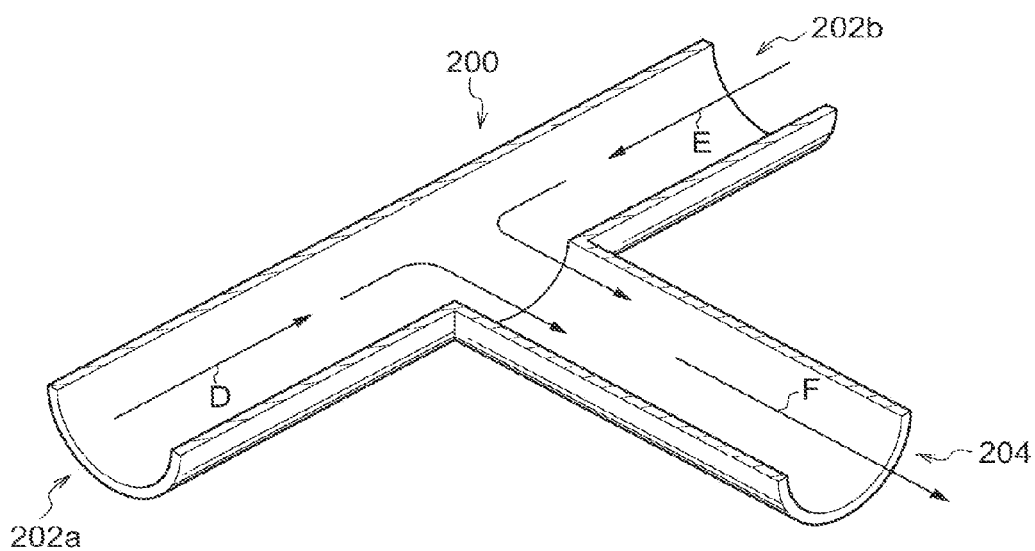
FIG. 2 is a schematic cross-sectional view of a T-shaped microreactor showing one example of mixing mechanism with a T-shaped microreactor.
Figure 3:
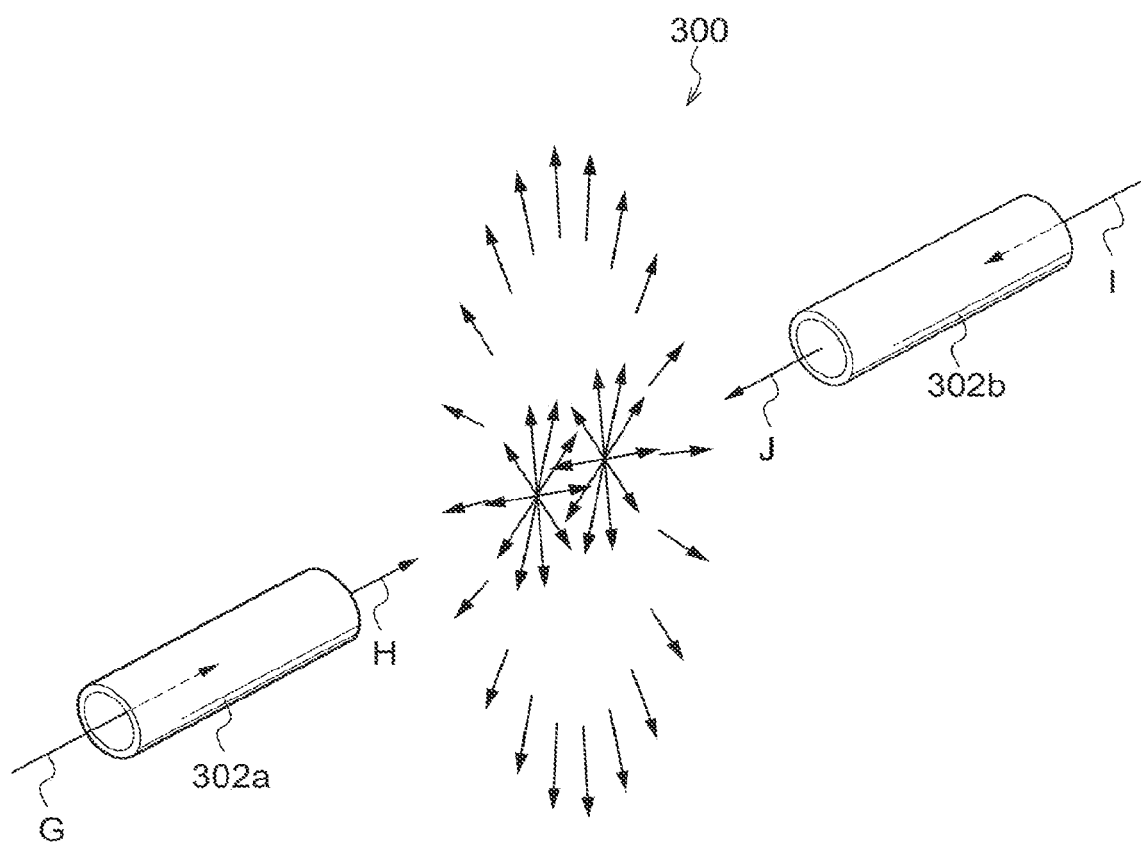
FIG. 3 is a conceptual view of a T-shaped microreactor showing one example of a mixing mechanism with a T-shaped microreactor.

FIG. 2 is a schematic cross-sectional view of T-type microreactor, showing one example of a mixing mechanism with a T-type microreactor. FIG. 3 is a conceptional view of a T-type microreactor, showing one example of a mixing mechanism with a T-type microreactor.

In FIG. 2, a cross-section of a T-type path 200 of a T-type microreactor is shown. In the T-type path 200, a fluid which has been flown therein in a direction of an arrow D through an inlet 202a, and a fluid which has been flown therein in a direction of an arrow E through an inlet 202b are collided at a central part in a path of the T-type path 200, and mixed to become a fine fluid particle. The fine fluid particle is flown out in a direction of an arrow F through an outlet 204. This T-type microreactor is useful for mixing when the volume of a path is small.

In FIG. 3, a fluid mixing mechanism (concept) 300 of other T-type microreactor is shown. In the fluid mixing mechanism shown in FIG. 3, fluids which have been flown therein through two paths 302a and 302b are mutually collided and mixed to become a fine fluid particle. That is, the fluid, on one hand, is flown in a path 302a in a direction of an arrow G, and is flown out in a direction of an arrow H. On the other hand, the fluid is flown in a path 302b in a direction of an arrow I, and is flown out in a direction of an arrow J. Fluids which have been flown out through paths 302a and 302b, respectively, are collided, are mixed, and are flied approximately orthogonal with a direction of an arrow G to J. The fluid mixing mechanism described in the path figure, FIG. 3, collides and mixes fluids diffused by a procedure of misting. By this collision and mixing, the fluid becomes finer, and a great contact surface may be obtained.

In the production method which may be applied to the method for producing the ceramide dispersion, it is preferable that a water-soluble organic solvent which has been used is removed after emulsification and dispersing through the micropath. As a method of removing a solvent, an evaporation method using a rotary evaporator, a flash evaporator, or an ultrasound atomizer, and a membrane separating method such as an ultrafiltration membrane and a reverse osmosis membrane are known, and an ultrafiltration membrane method is particularly preferable.

An ultra filter (abbreviated as UF) is an apparatus by which a stock solution (water, mixed aqueous solution of high-molecular substance, low-molecular substance, and colloidal substance) is pressurized, and water is poured into a UF apparatus, thereby, the stock solution may be separated into two-system solutions of a permeated solution (low-molecular substance) and a concentrated solution (high-molecular substance, colloidal substance), and taken out.

The ultrafiltration membrane is a typical asymmetric membrane made by the Leob-Sourirajan method. The polymer material used includes polyacrylonitrile, polyvinyl chloride-polyacrylonitrile copolymer, polysulfone, polyether sulfone, vinylidene fluoride, aromatic polyamide, or cellulose acetate, or the like. Recently, a ceramic membrane has become to be used. Unlike a reverse osmosis method, in an ultrafiltration method, since pre-treatment is not performed, fouling occurs, in which a polymer is deposited on a membrane surface. For this reason, it is normal to wash the membrane with a chemical or warm water periodically. For this reason, a membrane material is required to have resistance to a chemical and heat resistance. As a membrane module of an ultrafiltration membrane, there are various kinds such as flat membrane type, tubular type, hollow thread type, and spiral type. An index for performance of an ultrafiltration membrane is a fractionation molecular weight, and various membranes having a fractionation molecular weight of 1,000 to 300,000 are commercially available. As the commercially available membrane module, there are Microsa UF (Asahi Kasei Chemicals Corporation), and capillary-type element (trade name: NTU-3306, manufactured by Nitto Denko Corporation), being not limiting.

For removing a solvent from the obtained emulsion, a material of a membrane is particularly preferably polysulfone, polyether sulfone, or aromatic polyamide are particularly preferable from a viewpoint of solvent resistance. As the form of a membrane module, a flat membrane is mainly used at a laboratory scale, and a hollow shred type and spiral type are industrially used, and a hollow shred type is particularly preferable. In addition, a fraction molecular weight is different depending on a kind of an active component and, usually, the range of 5,000 to 100,000 is used.

An operation temperature may be 0° C. to 80° C. and, in view of degradation of an active component, the range of 10° C. to 40° C. is particularly preferable.

As an ultrafiltration device at a laboratory scale, there are ADVANTEC-UHP (ADVANTEC), Flow Type Labotest Unit RUM-2 (Nitto Denko Corporation) using and a flat membrane-typed module. Industrially, respective membrane modules at the size and the number depending on the necessary potency may be arbitrarily combined to construct a plant. As a bench scale unit, RUW-5A (Nitto Denko Corporation) is commercially available.

In the production method which may be applied to the method for producing the ceramide dispersion of the present invention, a process of concentrating the resulting emulsion subsequent to solvent removal may be added. As the concentrating method, the same method and the device as those of solvent removal such as an evaporation method and a filtration membrane method may be used. Also in the case of concentration, an ultrafiltration membrane method is a preferable method. When the same membrane as that of solvent removal may be used, this is preferable and, if necessary, ultrafiltration membranes having different fractionation molecular weights may be also used. Alternatively, a concentration efficacy may be enhanced by operating at a temperature different from that of solvent removal.

The ceramide dispersion (emulsion) obtained by mixing using the above-mentioned micromixer is oil-in-water emulsion. In the production method of a composition for external use of the present invention, a volume average particle diameter (median diameter) of dispersed particles of the emulsion is from 1 nm to 100 nm. From the viewpoint of transparency of the obtained emulsion, the diameter is more preferably from 1 nm to 50 nm.

The particle diameter of natural ceramide-containing particle (dispersed particle) can be measured by commercially available particle size distribution meter or the like, and details thereof are as described above.

<Application>

The ceramide dispersion of the present invention can be formed as fine emulsion which has an excellent emollient effect caused by natural ceramide. For this reason, the ceramide dispersion is preferably used as it is or as a component material for a variety of applications according to the functionality of the natural ceramide.

For such applications, the dispersion can be used widely, for example, as pharmaceuticals (external preparations, skin preparations), cosmetics and foods. Here, examples of the pharmaceuticals include parenteral agents such as suppositories and embrocations, and examples of the cosmetics include skin-care cosmetics (skin lotion, essence, milky lotion, cream or the like), sunscreen cosmetics and make-up cosmetics such as lipstick and foundation, but not limited thereto.

When the ceramide dispersion of the present invention is used for external preparations for skin or cosmetics, components which may be added to pharmaceuticals or cosmetics can be suitably added as required.

When the ceramide dispersion of the present invention is used for water-based products such as skin lotion, essence, milky lotion, cream mask pack, pack, shampoo cosmetics, fragrance cosmetics, liquid body shampoo, UV care cosmetics, deodorizing cosmetics, oral care cosmetics, analgesic- or antiphlogistic-containing gel, a medicinal component-containing layer of antiphlogistic-containing patch, a translucent product is obtained and occurrence of disadvantageous events can be inhibited such as deposition of insoluble matter, precipitation or neck ring under severe conditions such as long-term preservation or sterilization.

EXAMPLES

The present invention will be further specifically explained below by way of Examples, but the invention is not limited to the following Examples as far as it is not departed from the gist thereof. Unless otherwise is indicated, "part" is on a mass basis.

Example 1

All components described in "composition of oil phase liquid 1" below were stirred for one hour at room temperature to prepare an oil phase liquid 1.

| <Composition of oil phase liquid 1> | |
| --- | --- |
| Ceramide 3B [Natural ceramide, concrete examples 1-10] | 0.9 parts |
| Ceramide 6 [Natural ceramide, concrete examples 1-7] | 1.1 parts |
| Oleic acid (melting point: 14° C.) | 0.2 parts |
| Ethanol [water-soluble organic solvent] | 76.0 parts |

| <Composition of aqueous phase liquid 1> | |
| --- | --- |
| Pure water | |
| 0.1 molar sodium hydroxide | moderate amount |

Each of the obtained oil phase liquid 1 (oil phase) and water (aqueous phase) was heated to 30° C., and these were micro-mixed at a rate of 1:7 (mass ratio) by using KM-type micromixer 100/100, which is a counter-collision micromixer, thereby to obtain ceramide dispersion liquid 1 having a temperature of 30° C. The operating conditions for the micromixer were as follows:
—Micro Channel—
Oil Phase Side Micro Channel
Cross-sectional phase/width/depth/length=rectangular/70 μm/100 μm/10 mm
Aqueous Phase Side Micro Channel
Cross-sectional phase/width/depth/length=rectangular/490 μm/100 μm/10 mm
—Flow Rate—
An aqueous phase was introduced into an external annulus at the flow rate of 21.0 ml/min, an oil phase was introduced into an internal annulus at the flow rate of 3.0 ml/min, and these were micro-mixed.

The resulting ceramide dispersion liquid 1 was repeatedly desolvated to the ethanol concentration of 0.1% by mass or less using EVAPOR (CEP-lab) manufactured by OKAWARA CORPORATION, and this was concentrated and adjusted to the ceramide concentration of 1.0% by mass to obtain a ceramide dispersion A having a pH of 7.3. The ceramide concentration referred herein is the content of the ceramide analog based on the total mass of the ceramide dispersion.

Example 2

The same procedures as in Example 1 were repeated except that the oil phase liquid 1 was changed to the oil phase liquid 2 below and that each of the obtained oil phase liquid 2 (oil phase) and water (aqueous phase) was heated to 40° C., to obtain ceramide dispersion liquid 2. Ceramide dispersion liquid 2 was concentrated and adjusted in the same manner as in Example 1, to obtain ceramide dispersion B having a pH of 6.2.

| <Composition of oil phase liquid 2> | |
| --- | --- |
| Ceramide 3B [Natural ceramide, concrete examples 1-10] | 0.9 parts |
| Ceramide 6 [Natural ceramide, concrete examples 1-7] | 1.1 parts |
| Isostearic acid (melting point: –10° C.) | 2.0 parts |
| Ethanol [water-soluble organic solvent] | 76.0 parts |

Example 3

The same procedures as in Example 1 were repeated except that the oil phase liquid 1 was changed to the oil phase liquid 3 below and that each of the obtained oil phase liquid 3 (oil phase) and water (aqueous phase) was heated to 25° C., to obtain ceramide dispersion liquid 3. Ceramide dispersion liquid 3 was concentrated and adjusted in the same manner as in Example 1, to obtain ceramide dispersion C having a pH of 7.9.

| <Composition of oil phase liquid 3> | |
| --- | --- |
| Ceramide 3B [Natural ceramide, concrete examples 1-10] | 0.9 parts |
| Ceramide 6 [Natural ceramide, concrete examples 1-7] | 1.1 parts |
| Linoleic acid (melting point: 5° C.) | 1.0 parts |
| Ethanol [water-soluble organic solvent] | 76.0 parts |

Example 4

The same procedures as in Example 1 were repeated except that the oil phase liquid 1 was changed to the oil phase liquid 4 below and that each of the obtained oil phase liquid 4 (oil phase) and water (aqueous phase) was heated to 20° C., to obtain ceramide dispersion liquid 4. Ceramide dispersion liquid 4 was concentrated and adjusted in the same manner as in Example 1, to obtain ceramide dispersion D having a pH of 7.2.

| <Composition of oil phase liquid 4> | |
| --- | --- |
| Ceramide 3B [Natural ceramide, concrete examples 1-10] | 0.9 parts |
| Ceramide 6 [Natural ceramide, concrete examples 1-7] | 1.1 parts |
| α-Linolenic acid (melting point: –11° C.) | 0.4 parts |
| Ethanol [water-soluble organic solvent] | 76.0 parts |

Example 5

The same procedures as in Example 1 were repeated except that the oil phase liquid 1 was changed to the oil phase liquid 5 below and that each of the obtained oil phase liquid 5 (oil phase) and water (aqueous phase) was heated to 30° C., to obtain ceramide dispersion liquid 5. Ceramide dispersion liquid 5 was concentrated and adjusted in the same manner as in Example 1, to obtain ceramide dispersion E having a pH of 7.

| <Composition of oil phase liquid 5> | |
| --- | --- |
| Ceramide 3B [Natural ceramide, concrete examples 1-10] | 0.9 parts |
| Ceramide 6 [Natural ceramide, concrete examples 1-7] | 1.1 parts |
| Arachidonic acid (melting point: –49.5° C.) | 0.02 parts |
| Ethanol [water-soluble organic solvent] | 76.0 parts |

Example 6

The same procedures as in Example 1 were repeated except that the oil phase liquid 1 was changed to the oil phase liquid 6 below, that the aqueous phase liquid 1 was changed to the aqueous phase liquid 6 below and that each of the obtained oil phase liquid 6 (oil phase) and aqueous phase liquid 6 (aqueous phase) was heated to 33° C., to obtain ceramide dispersion liquid 6. Ceramide dispersion liquid 6 was concentrated and adjusted in the same manner as in Example 1, to obtain a ceramide dispersion F having a pH of 7.1.

<Composition of oil phase liquid 6>

| | |
|---|---|
| Ceramide 3B [Natural ceramide, concrete examples 1-10] | 0.9 parts |
| Ceramide 6 [Natural ceramide, concrete examples 1-7] | 1.1 parts |
| Ethanol [water-soluble organic solvent] | 76.0 parts |

<Composition of aqueous phase liquid 6>

| | |
|---|---|
| Pure water | 99.95 parts |
| Sodium oleate (melting point: 232 to 235° C.) | 0.06 parts |
| 0.1 molar sodium hydroxide | moderate amount |

Example 7

The same procedures as in Example 1 were repeated except that the oil phase liquid 1 was changed to the oil phase liquid 7 below and that each of the obtained oil phase liquid 7 (oil phase) and water (aqueous phase) was heated to 32° C., to obtain ceramide dispersion liquid 7. Ceramide dispersion liquid 7 was concentrated and adjusted in the same manner as in Example 1, to obtain ceramide dispersion G having a pH of 7.3.

<Composition of oil phase liquid 7>

| | |
|---|---|
| Ceramide 3B [Natural ceramide, concrete examples 1-10] | 0.9 parts |
| Ceramide 6 [Natural ceramide, concrete examples 1-7] | 1.1 parts |
| Oleic acid (melting point: 14° C.) | 0.1 parts |
| Decaglyceryl oleate (HLB = 12) | 0.1 parts |
| Ethanol [water-soluble organic solvent] | 76.0 parts |

Example 8

The same procedures as in Example 1 were repeated except that the oil phase liquid 1 was changed to the oil phase liquid 8 below and that each of the obtained oil phase liquid 8 (oil phase) and water (aqueous phase) was heated to 31° C., to obtain ceramide dispersion liquid 8. Ceramide dispersion liquid 8 was concentrated and adjusted in the same manner as in Example 1, to obtain ceramide dispersion H having a pH of 7.5.

<Composition of oil phase liquid 8>

| | |
|---|---|
| Ceramide 3B [Natural ceramide, concrete examples 1-10] | 0.9 parts |
| Ceramide 6 [Natural ceramide, concrete examples 1-7] | 1.1 parts |
| Oleic acid (melting point: 14° C.) | 1.0 parts |
| Ethanol [water-soluble organic solvent] | 76.0 parts |

Example 9

The same procedures as in Example 1 were repeated except that the oil phase liquid 1 was changed to the oil phase liquid 9 below and that each of the obtained oil phase liquid 9 (oil phase) and water (aqueous phase) was heated to 32° C., to obtain ceramide dispersion liquid 9. Ceramide dispersion liquid 9 was concentrated and adjusted in the same manner as in Example 1, to obtain ceramide dispersion I having a pH of 7.

<Composition of oil phase liquid 9>

| | |
|---|---|
| Ceramide 3B [Natural ceramide, concrete examples 1-10] | 0.9 parts |
| Ceramide 6 [Natural ceramide, concrete examples 1-7] | 1.1 parts |
| Eicosapentaenoic acid (melting point: −54° C.) | 0.02 parts |
| Ethanol [water-soluble organic solvent] | 76.0 parts |

Comparative Example 1

The same procedures as in Example 1 were repeated except that the oil phase liquid 1 was changed to the oil phase liquid 10 below and that each of the obtained oil phase liquid 10 (oil phase) and water (aqueous phase) was heated to 60° C., to obtain ceramide dispersion liquid 10. Ceramide dispersion liquid 10 was concentrated and adjusted in the same manner as in Example 1, to obtain ceramide dispersion K having a pH of 7.1.

<Composition of oil phase liquid 10>

| | |
|---|---|
| Ceramide 3B [Natural ceramide, concrete examples 1-10] | 0.9 parts |
| Ceramide 6 [Natural ceramide, concrete examples 1-7] | 1.1 parts |
| Myristic acid (melting point: 53.9° C.) | 2.4 parts |
| Ethanol [water-soluble organic solvent] | 76.0 parts |

Comparative Example 2

The same procedures as in Example 1 were repeated except that the oil phase liquid 1 was changed to the oil phase liquid 11 below and that each of the obtained oil phase liquid 11 (oil phase) and water (aqueous phase) was heated to 60° C., to obtain ceramide dispersion liquid 11. Ceramide dispersion liquid 11 was concentrated and adjusted in the same manner as in Example 1, to obtain ceramide dispersion L having a pH of 7.

<Composition of oil phase liquid 11>

| | |
|---|---|
| Ceramide 3B [Natural ceramide, concrete examples 1-10] | 0.9 parts |
| Ceramide 6 [Natural ceramide, concrete examples 1-7] | 1.1 parts |
| POE (20) sorbitan monooleate | 4.0 parts |
| Ethanol [water-soluble organic solvent] | 76.0 parts |

Comparative Example 3

The same procedures as in Example 1 were repeated except that the oil phase liquid 1 was changed to oil phase liquid 12 having the same composition as the oil phase liquid 1, that the aqueous phase liquid 1 was changed to aqueous phase liquid 12 which does not contain 0.1 molar sodium hydroxide, and that each of these was heated to 31° C., to obtain ceramide dispersion liquid 12. Ceramide dispersion liquid 12 was concentrated and adjusted in the same manner as in Example 1, to obtain a ceramide dispersion M having a pH of 5.8.

Comparative Example 4

The same procedures as in Example 1 were repeated except that the oil phase liquid 1 was changed to oil phase liquid 13 having the same composition as the oil phase liquid 1, that the aqueous phase liquid 1 was changed to the aqueous phase liquid 13 below and that each of the obtained aqueous phase liquid 13 (aqueous phase) and oil phase liquid 13 was heated to 32° C., to obtain ceramide dispersion liquid 13. Ceramide dispersion liquid 13 was concentrated and adjusted in the same manner as in Example 1, to obtain a ceramide dispersion N having a pH of 8.5.

| <Composition of aqueous phase liquid 13> | |
| --- | --- |
| Pure water | |
| 0.1 molar sodium hydroxide | moderate amount |
| (pH of Final ceramide dispersion N: 8.5) | |

Comparative Example 5

The same procedures as in Example 1 were repeated except that the oil phase liquid I was changed to oil phase liquid 14 having the same composition as the oil phase liquid 1, that the aqueous phase liquid 1 was changed to the aqueous phase liquid 14 below and that each of the obtained aqueous phase liquid 14 (aqueous phase) and oil phase liquid 14 (oil phase) was heated to 32° C., to obtain ceramide dispersion liquid 14. Ceramide dispersion liquid 14 was concentrated and adjusted in the same manner as in Example 1, to obtain a ceramide dispersion O having a pH of 7.1.

| <Composition of aqueous phase liquid 14> | |
| --- | --- |
| Pure water | 99.92 parts |
| Sucrose laurate | 0.19 parts |
| 0.1 molar sodium hydroxide | moderate amount |

Comparative Example 6

The same procedures as in Example 1 were repeated except that the oil phase liquid 1 was changed to oil phase liquid 15 having the same composition as the oil phase liquid 1, that the aqueous phase liquid 1 was changed to the aqueous phase liquid 15 below and that each of the obtained aqueous phase liquid 15 (aqueous phase) and oil phase liquid 15 (oil phase) was heated to 33° C., to obtain ceramide dispersion liquid 15. Ceramide dispersion liquid 15 was concentrated and adjusted in the same manner as in Example 1, to obtain a ceramide dispersion P having a pH of 7.5.

| <Composition of aqueous phase liquid 15> | |
| --- | --- |
| Pure water | 99.92 parts |
| Hydrogenated lecithin [ionic surfactant] | 0.02 parts |
| 0.1 molar sodium hydroxide | moderate amount |

Comparative Example 7

The same procedures as in Example 1 were repeated except that the oil phase liquid 1 was changed to the oil phase liquid 16 below and that each of the obtained oil phase liquid 16 (oil phase) and water (aqueous phase) was heated to 60° C., to obtain ceramide dispersion liquid 16. Ceramide dispersion liquid 16 was concentrated and adjusted in the same manner as in Example 1, to obtain a ceramide dispersion Q having a pH of 7.4.

| <Composition of oil phase liquid 16> | |
| --- | --- |
| Ceramide 3B [Natural ceramide, concrete examples 1-10] | 0.9 parts |
| Ceramide 6 [Natural ceramide, concrete examples 1-7] | 1.1 parts |
| Oleic acid (melting point: 14° C.) | 2.4 parts |
| Ethanol [water-soluble organic solvent] | 76.0 parts |

Comparative Example 8

The same procedures as in Example 1 were repeated except that each of the oil phase liquid 1 and the aqueous phase liquid 1 was heated to 49° C., to obtain ceramide dispersion liquid 17. Ceramide dispersion liquid 17 was concentrated and adjusted in the same manner as in Example 1, to obtain a ceramide dispersion R having a pH of 7.4.

<Evaluation>

1. Particle Diameter of Ceramide-Containing Particle

The particle diameter (volume average particle diameter) of the ceramide-containing particle (or oil droplet-like dispersion particles containing the same) in ceramide dispersion immediately after preparation was measured using a dynamic light scattering particle size distribution meter LB-550 (manufactured by HORIBA Ltd.). In the measurement of the particle diameter, the natural ceramide-containing particles were diluted with pure water so as to have a concentration of 1% by mass, and the particle diameter was measured using quartz cell. The particle diameter was determined as a median diameter when the refractive index of a sample was 1.600, the refractive index of a dispersion medium was 1.333 (pure water), and the viscosity of pure water was set as the viscosity of the dispersion medium. The results are shown in Table 1.

2. Evaluation of Stability of Ceramide Dispersion Over Time

As the evaluation of stability over time, an evaluation was performed using turbidity by the following method.

Turbidities of the ceramide dispersion A to ceramide dispersion I of Examples and Comparative Examples were measured as the absorbance at 660 nm in 10 mm cell using UV VIBLE Spectrophotometer UV-2550 (manufactured by Simadzu Corporation). (measurement temperature: 25° C.)

Further, each of the ceramide dispersions was stored in a temperature-controlled bath at 40° C. for one month, and then reset the ceramide dispersions at 25° C. to measure the turbidities. The results are shown in Table 1.

3. Observation of External Appearance

The external appearance was observed in terms of the existence or absence of a fine precipitate of the ceramide dispersion and the uniformity of the dispersion liquid, immediately after the ceramide dispersion was prepared and after the ceramide dispersion had been stored in a temperature-controlled bath at 40° C. for one month. Evaluation was performed in the following manner:

A: The whole dispersion was uniform without a precipitate, or no change was observed in the external appearance compared with immediately after the dispersion was prepared.

B: No precipitate, but somewhat poor in transparency.

C: Precipitate, occurrence of separation in the dispersion liquid, or change in the external appearance after one month at 40° C. as compared with immediately after the preparation (unacceptable in terms of commercial value).

TABLE 1

| | Ceramide dispersion | Fatty acid ingredient | Melting point of fatty acid | Fatty acid (salt)/ Ceramide | (Non-)ionic surfactant | (Non-)ionic surfactant/ Ceramide | pH of dispersion |
|---|---|---|---|---|---|---|---|
| Example 1 | Ceramide dispersion A | Oleic acid | 14° C. | 0.1 | | | 7.3 |
| Example 2 | Ceramide dispersion B | Isostearic acid | −10° C. | 1 | | | 6.2 |
| Example 3 | Ceramide dispersion C | Linoleic acid | 5° C. | 0.5 | | | 7.9 |
| Example 4 | Ceramide dispersion D | α-Linolenic acid | −11° C. | 0.2 | | | 7.2 |
| Example 5 | Ceramide dispersion E | Arachidonic acid | −49.5° C. | 0.01 | | | 7 |
| Example 6 | Ceramide dispersion F | Sodium oleate | 232~235° C. | 0.15 | | | 7.1 |
| Example 7 | Ceramide dispersion G | Oleic acid | 14° C. | 0.05 | Decaglyceryl oleate | 0.05 | 7.3 |
| Example 8 | Ceramide dispersion H | Oleic acid | 14° C. | 0.5 | | | 7.5 |
| Example 9 | Ceramide dispersion I | Eicosapentaenoic acid | −54° C. | 0.01 | | | 7 |
| Comparative Example 1 | Ceramide dispersion K | Myristic acid | 53.9° C. | 1.2 | | | 7.1 |
| Comparative Example 2 | Ceramide dispersion L | | | | POE (20) sorbitan monooleate | 2.0 | 7 |
| Comparative Example 3 | Ceramide dispersion M | Oleic acid | 14° C. | 0.1 | | | 5.8 |
| Comparative Example 4 | Ceramide dispersion N | Oleic acid | 14° C. | 0.1 | | | 8.5 |
| Comparative Example 5 | Ceramide dispersion O | Oleic acid | 14° C. | 0.1 | Sucrose laurate | 0.5 | 7.1 |
| Comparative Example 6 | Ceramide dispersion P | Oleic acid | 14° C. | 0.1 | Hydrogenated lecithin | 0.05 | 7.5 |
| Comparative Example 7 | Ceramide dispersion Q | Oleic acid | 14° C. | 0.15 | | | 7.4 |
| Comparative Example 8 | Ceramide dispersion R | Oleic acid | 14° C. | 0.1 | | | 7.4 |

| | Temperature at dispersion | Physical properties immediately after preparation | | Physical properties after one month at 40° C. | | Outer appearance evaluation |
|---|---|---|---|---|---|---|
| | | Average particle diameter (nm) | Absorbance at 660 nm | Average particle diameter (nm) | Absorbance at 660 nm | |
| Example 1 | 30° C. | 1.5 | 0.007 | 1.6 | 0.008 | A |
| Example 2 | 40° C. | 2.5 | 0.031 | 11.5 | 0.038 | A |
| Example 3 | 25° C. | 2.1 | 0.021 | 2.2 | 0.024 | A |
| Example 4 | 20° C. | 28.3 | 0.018 | 25.1 | 0.014 | A |
| Example 5 | 30° C. | 88.2 | 0.048 | 90.1 | 0.050 | A |
| Example 6 | 33° C. | 1.6 | 0.009 | 1.8 | 0.011 | A |
| Example 7 | 32° C. | 3.8 | 0.011 | 4 | 0.014 | A |
| Example 8 | 31° C. | 1.9 | 0.016 | 2.2 | 0.023 | A |
| Example 9 | 32° C. | 53.7 | 0.028 | 52.9 | 0.027 | A |
| Comparative Example 1 | 60° C. | 185.5 | Cloudy | Not available | Cloudy and separated | C |
| Comparative Example 2 | 60° C. | 159.3 | 0.088 | 180.3 | Cloudy and separated | C |
| Comparative Example 3 | 31° C. | 1.8 | 0.008 | Not available | Cloudy and separated | C |
| Comparative Example 4 | 32° C. | 1.7 | 0.011 | 31.8 | 0.128 | C |
| Comparative Example 5 | 32° C. | 162.8 | 0.189 | Not available | Cloudy and separated | C |
| Comparative Example 6 | 33° C. | Not available | Cloudy | Cancelled | Cancelled | C |
| Comparative Example 7 | 60° C. | 123.5 | Cloudy | Not available | Cloudy and separated | B |
| Comparative Example 8 | 49° C. | 10.8 | 0.0018 | Filamentous precipitate | Cloudy and separated | C |

As is apparent from Table 1, it was seen that the particle diameter of the ceramide-containing particle contained in the ceramide dispersion of the present invention was small, and that the ceramide dispersion of the present invention had favorable dispersion stability and favorable stability over time.

In Comparative Example 4 in which the pH was not lower than 8, the ceramide dispersion had poor transparency and a precipitate was also observed in the evaluation of the external appearance of the ceramide dispersion after one month. Further, it was apparent that the viscosity of the dispersion would increase, and the dispersion would be gelled, and therefore, the dispersion would have poor stability over time. Likewise, in Comparative Example 6 in which lecithin, which corresponds to an ionic surfactant, was contained in an amount which was 0.05 times the amount of the ceramide, since the ceramide dispersion had poor solubility in ethanol and in a water solvent at a dispersion temperature of 33° C., the ceramide dispersion became cloudy immediately after mixing, and therefore, it was apparent that the ceramide dispersion would have poor dispersion stability. In Comparative Example 6, although the lecithin would be dissolved if the dispersion temperature was set at not lower than 40° C., the particle diameter would increase and the dispersion would have poor transparency and poor stability over time.

The disclosure of Japanese Patent Application No. 2008-255079, which was filed on Sep. 30, 2008, is hereby incorporated by reference in its entirety.

All references, patent applications, and technical standards described in the present specification are herein incorporated in their entirety by reference into the specification, to the same extent as if each individual reference, patent application or technical standard was specifically and individually indicated to be incorporated herein by reference.

What is claimed:

1. A ceramide dispersion comprising:
   (1) ceramide-containing particles which contain a ceramide, which are dispersed in an aqueous phase as an oil-phase component, and which have a volume average particle diameter from 1 nm to 100 nm;
   (2) a fatty acid component which is at least one selected from the group consisting of lauric acid, isostearic acid, oleic acid, γ-linolenic acid, α-linolenic acid, linoleic acid and salts thereof, and
   (3) at least one nonionic surfactant selected from the group consisting of glycerol fatty acid esters, organic acid monoglycerides, polyglycerol fatty acid esters, propylene glycol fatty acid esters, polyglycerol condensation ricinolein acid esters, sorbitan fatty acid esters and sucrose fatty acid esters and polyoxyethylene sorbitan fatty acid esters,
   the amount of the nonionic surfactant being not more than 0.1 times a total mass of the ceramide; the amount of an ionic surfactant other than the fatty acid component being 0 or less than 0.05 times the total mass of the ceramide; and pH being from 6.2 to 8.

2. The ceramide dispersion according to claim 1, having absorbance at 660 nm of not higher than 0.050.

3. The ceramide dispersion according to claim 1, wherein the fatty acid component is contained in an amount of from 0.01 to 1.0 times the total mass of the ceramide.

4. The ceramide dispersion according to claim 1, wherein a content of the ceramide is from 0.1% by mass to 3% by mass of a total mass of the ceramide dispersion.

5. The ceramide dispersion according to claim 1, wherein the pH is from 7 to less than 8.

6. The ceramide dispersion according to claim 1, wherein the nonionic surfactant is a polyglycerol fatty acid ester.

7. The ceramide dispersion according to claim 6, wherein the polyglycerol fatty acid ester is a polyglycerol fatty acid ester having an HLB of from 10 to 16.

8. The ceramide dispersion according to claim 6, wherein the polyglycerol fatty acid ester is an ester of a polyglycerine having an average degree of polymerization of 10 and a carbon number of the fatty acid of from 8 to 10.

9. A method for producing the ceramide dispersion according to claim 1, the method comprising:
   mixing an oil phase component containing the ceramide, the fatty acid component, and at least one non-ionic surfactant with an aqueous phase component at a temperature not higher than 40° C.

10. The method for producing the ceramide dispersion according to claim 9, the method comprising dissolving the ceramide in a water-soluble organic solvent.

11. The method for producing the ceramide dispersion according to claim 9, wherein the mixing of the oil phase component with the aqueous phase component is performed by combining the oil phase component and the aqueous phase component after passing the oil phase component and the aqueous phase component individually through flow channels, the flow channels having sectional areas at a narrowest portion of from 1 μm$^2$ to 1 mm$^2$.

* * * * *